United States Patent
Roy

(10) Patent No.: US 10,293,108 B2
(45) Date of Patent: May 21, 2019

(54) INFUSION DEVICES AND RELATED PATIENT RATIO ADJUSTMENT METHODS

(71) Applicant: MEDTRONIC MINIMED, INC., Northridge, CA (US)

(72) Inventor: Anirban Roy, Calabasas, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 342 days.

(21) Appl. No.: 15/096,142

(22) Filed: Apr. 11, 2016

(65) Prior Publication Data

US 2017/0049961 A1 Feb. 23, 2017

Related U.S. Application Data

(60) Provisional application No. 62/208,454, filed on Aug. 21, 2015.

(51) Int. Cl.
*A61M 5/172* (2006.01)
*A61M 5/145* (2006.01)
*A61M 5/142* (2006.01)

(52) U.S. Cl.
CPC ........ *A61M 5/1723* (2013.01); *A61M 5/1452* (2013.01); *A61M 2005/14208* (2013.01);
(Continued)

(58) Field of Classification Search
CPC .............. A61M 5/1723; A61M 5/1452; A61M 2230/201; A61M 2230/005;
(Continued)

(56) References Cited

U.S. PATENT DOCUMENTS 3,631,847 A 1/1972 Hobbs, II
4,212,738 A 7/1980 Henne
(Continued)

FOREIGN PATENT DOCUMENTS

DE 4329229 3/1995
EP 0319268 11/1988
(Continued)

OTHER PUBLICATIONS

PCT Search Report (PCT/US02/03299), dated Oct. 31, 2002, Medtronic Minimed, Inc.
(Continued)

*Primary Examiner* — Amber R Stiles
(74) *Attorney, Agent, or Firm* — Lorenz & Kopf, LLP

(57) ABSTRACT

Infusion systems, infusion devices, and related operating methods are provided. An exemplary method of operating an infusion device to deliver a bolus amount of fluid influencing a physiological condition in a body of a user involves identifying, based on measurement values for the physiological condition, a residual value for the physiological condition resulting from the bolus amount of the fluid and determining an updated ratio for a subsequent bolus by adjusting an initial ratio influencing the bolus amount to compensate for the residual value. The updated ratio may be stored in a data storage element for use in determining a subsequent bolus amount in lieu of the initial ratio value.

14 Claims, 8 Drawing Sheets

(52) U.S. Cl.
CPC ... *A61M 2205/50* (2013.01); *A61M 2205/502* (2013.01); *A61M 2205/52* (2013.01); *A61M 2205/702* (2013.01); *A61M 2230/005* (2013.01); *A61M 2230/201* (2013.01)

(58) Field of Classification Search
CPC ........ A61M 2205/52; A61M 2205/502; A61M 2205/50; A61M 2205/702; A61M 2005/14208
See application file for complete search history.

(56) References Cited

U.S. PATENT DOCUMENTS

| | | |
|---|---|---|
| 4,270,532 A | 6/1981 | Franetzki et al. |
| 4,282,872 A | 8/1981 | Franetzki et al. |
| 4,373,527 A | 2/1983 | Fischell |
| 4,395,259 A | 7/1983 | Prestele et al. |
| 4,433,072 A | 2/1984 | Pusineri et al. |
| 4,443,218 A | 4/1984 | Decant, Jr. et al. |
| 4,494,950 A | 1/1985 | Fischell |
| 4,542,532 A | 9/1985 | McQuilkin |
| 4,550,731 A | 11/1985 | Batina et al. |
| 4,559,037 A | 12/1985 | Franetzki et al. |
| 4,562,751 A | 1/1986 | Nason et al. |
| 4,671,288 A | 6/1987 | Gough |
| 4,678,408 A | 7/1987 | Nason et al. |
| 4,685,903 A | 8/1987 | Cable et al. |
| 4,731,051 A | 3/1988 | Fischell |
| 4,731,726 A | 3/1988 | Allen, III |
| 4,781,798 A | 11/1988 | Gough |
| 4,803,625 A | 2/1989 | Fu et al. |
| 4,809,697 A | 3/1989 | Causey, III et al. |
| 4,826,810 A | 5/1989 | Aoki |
| 4,871,351 A | 10/1989 | Feingold |
| 4,898,578 A | 2/1990 | Rubalcaba, Jr. |
| 5,003,298 A | 3/1991 | Havel |
| 5,011,468 A | 4/1991 | Lundquist et al. |
| 5,019,974 A | 5/1991 | Beckers |
| 5,050,612 A | 9/1991 | Matsumura |
| 5,078,683 A | 1/1992 | Sancoff et al. |
| 5,080,653 A | 1/1992 | Voss et al. |
| 5,097,122 A | 3/1992 | Colman et al. |
| 5,100,380 A | 3/1992 | Epstein et al. |
| 5,101,814 A | 4/1992 | Palti |
| 5,108,819 A | 4/1992 | Heller et al. |
| 5,153,827 A | 10/1992 | Coutre et al. |
| 5,165,407 A | 11/1992 | Wilson et al. |
| 5,247,434 A | 9/1993 | Peterson et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,284,140 A | 2/1994 | Allen et al. |
| 5,299,571 A | 4/1994 | Mastrototaro |
| 5,307,263 A | 4/1994 | Brown |
| 5,317,506 A | 5/1994 | Coutre et al. |
| 5,320,725 A | 6/1994 | Gregg et al. |
| 5,322,063 A | 6/1994 | Allen et al. |
| 5,338,157 A | 8/1994 | Blomquist |
| 5,339,821 A | 8/1994 | Fujimoto |
| 5,341,291 A | 8/1994 | Roizen et al. |
| 5,350,411 A | 9/1994 | Ryan et al. |
| 5,356,786 A | 10/1994 | Heller et al. |
| 5,357,427 A | 10/1994 | Langen et al. |
| 5,368,562 A | 11/1994 | Blomquist et al. |
| 5,370,622 A | 12/1994 | Livingston et al. |
| 5,371,687 A | 12/1994 | Holmes, II et al. |
| 5,376,070 A | 12/1994 | Purvis et al. |
| 5,390,671 A | 2/1995 | Lord et al. |
| 5,391,250 A | 2/1995 | Cheney, II et al. |
| 5,403,700 A | 4/1995 | Heller et al. |
| 5,411,647 A | 5/1995 | Johnson et al. |
| 5,482,473 A | 1/1996 | Lord et al. |
| 5,485,408 A | 1/1996 | Blomquist |
| 5,497,772 A | 3/1996 | Schulman et al. |
| 5,505,709 A | 4/1996 | Funderburk et al. |
| 5,543,326 A | 8/1996 | Heller et al. |
| 5,569,186 A | 10/1996 | Lord et al. |
| 5,569,187 A | 10/1996 | Kaiser |
| 5,573,506 A | 11/1996 | Vasko |
| 5,582,593 A | 12/1996 | Hultman |
| 5,586,553 A | 12/1996 | Halili et al. |
| 5,593,390 A | 1/1997 | Castellano et al. |
| 5,593,852 A | 1/1997 | Heller et al. |
| 5,594,638 A | 1/1997 | Iliff |
| 5,609,060 A | 3/1997 | Dent |
| 5,626,144 A | 5/1997 | Tacklind et al. |
| 5,630,710 A | 5/1997 | Tune et al. |
| 5,643,212 A | 7/1997 | Coutre et al. |
| 5,660,163 A | 8/1997 | Schulman et al. |
| 5,660,176 A | 8/1997 | Iliff |
| 5,665,065 A | 9/1997 | Colman et al. |
| 5,665,222 A | 9/1997 | Heller et al. |
| 5,685,844 A | 11/1997 | Marttila |
| 5,687,734 A | 11/1997 | Dempsey et al. |
| 5,704,366 A | 1/1998 | Tacklind et al. |
| 5,750,926 A | 5/1998 | Schulman et al. |
| 5,754,111 A | 5/1998 | Garcia |
| 5,764,159 A | 6/1998 | Neftel |
| 5,772,635 A | 6/1998 | Dastur et al. |
| 5,779,665 A | 7/1998 | Mastrototaro et al. |
| 5,788,669 A | 8/1998 | Peterson |
| 5,791,344 A | 8/1998 | Schulman et al. |
| 581,401 A | 9/1998 | Gargano et al. |
| 5,800,420 A | 9/1998 | Gross et al. |
| 5,807,336 A | 9/1998 | Russo et al. |
| 5,822,715 A | 10/1998 | Worthington et al. |
| 5,832,448 A | 11/1998 | Brown |
| 5,840,020 A | 11/1998 | Heinonen et al. |
| 5,861,018 A | 1/1999 | Feierbach et al. |
| 5,868,669 A | 2/1999 | Iliff |
| 5,871,465 A | 2/1999 | Vasko |
| 5,879,163 A | 3/1999 | Brown et al. |
| 5,885,245 A | 3/1999 | Lynch et al. |
| 5,897,493 A | 4/1999 | Brown |
| 5,899,855 A | 5/1999 | Brown |
| 5,904,708 A | 5/1999 | Goedeke |
| 5,913,310 A | 6/1999 | Brown |
| 5,917,346 A | 6/1999 | Gord |
| 5,918,603 A | 7/1999 | Brown |
| 5,925,021 A | 7/1999 | Castellano et al. |
| 5,933,136 A | 8/1999 | Brown |
| 5,935,099 A | 8/1999 | Peterson et al. |
| 5,940,801 A | 8/1999 | Brown |
| 5,956,501 A | 9/1999 | Brown |
| 5,960,403 A | 9/1999 | Brown |
| 5,965,380 A | 10/1999 | Heller et al. |
| 5,972,199 A | 10/1999 | Heller et al. |
| 5,978,236 A | 11/1999 | Faberman et al. |
| 5,997,476 A | 12/1999 | Brown |
| 5,999,848 A | 12/1999 | Gord et al. |
| 5,999,849 A | 12/1999 | Gord et al. |
| 6,009,339 A | 12/1999 | Bentsen et al. |
| 6,032,119 A | 2/2000 | Brown et al. |
| 6,043,437 A | 3/2000 | Schulman et al. |
| 6,081,736 A | 6/2000 | Colvin et al. |
| 6,083,710 A | 7/2000 | Heller et al. |
| 6,088,608 A | 7/2000 | Schulman et al. |
| 6,101,478 A | 8/2000 | Brown |
| 6,103,033 A | 8/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,134,461 A | 10/2000 | Say et al. |
| 6,143,164 A | 11/2000 | Heller et al. |
| 6,162,611 A | 12/2000 | Heller et al. |
| 6,175,752 B1 | 1/2001 | Say et al. |
| 6,183,412 B1 | 2/2001 | Benkowski et al. |
| 6,246,992 B1 | 6/2001 | Brown |
| 6,248,093 B1 | 6/2001 | Moberg |
| 6,259,937 B1 | 7/2001 | Schulman et al. |
| 6,329,161 B1 | 12/2001 | Heller et al. |
| 6,408,330 B1 | 6/2002 | DeLaHuerga |
| 6,424,847 B1 | 7/2002 | Mastrototaro et al. |

(56) References Cited

U.S. PATENT DOCUMENTS

| | | |
|---|---|---|
| 6,472,122 B1 | 10/2002 | Schulman et al. |
| 6,484,045 B1 | 11/2002 | Holker et al. |
| 6,484,046 B1 | 11/2002 | Say et al. |
| 6,485,465 B2 | 11/2002 | Moberg et al. |
| 6,503,381 B1 | 1/2003 | Gotoh et al. |
| 6,514,718 B2 | 2/2003 | Heller et al. |
| 6,544,173 B2 | 4/2003 | West et al. |
| 6,553,263 B1 | 4/2003 | Meadows et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,560,741 B1 | 5/2003 | Gerety et al. |
| 6,565,509 B1 | 5/2003 | Say et al. |
| 6,579,690 B1 | 6/2003 | Bonnecaze et al. |
| 6,589,229 B1 | 7/2003 | Connelly et al. |
| 6,591,125 B1 | 7/2003 | Buse et al. |
| 6,592,745 B1 | 7/2003 | Feldman et al. |
| 6,605,200 B1 | 8/2003 | Mao et al. |
| 6,605,201 B1 | 8/2003 | Mao et al. |
| 6,607,658 B1 | 8/2003 | Heller et al. |
| 6,616,819 B1 | 9/2003 | Liamos et al. |
| 6,618,934 B1 | 9/2003 | Feldman et al. |
| 6,623,501 B2 | 9/2003 | Heller et al. |
| 6,641,533 B2 | 11/2003 | Causey, III et al. |
| 6,654,625 B1 | 11/2003 | Say et al. |
| 6,659,980 B2 | 12/2003 | Moberg et al. |
| 6,671,554 B2 | 12/2003 | Gibson et al. |
| 6,676,816 B2 | 1/2004 | Mao et al. |
| 6,689,265 B2 | 2/2004 | Heller et al. |
| 6,728,576 B2 | 4/2004 | Thompson et al. |
| 6,733,471 B1 | 5/2004 | Ericson et al. |
| 6,740,072 B2 | 5/2004 | Starkweather et al. |
| 6,746,582 B2 | 6/2004 | Heller et al. |
| 6,747,556 B2 | 6/2004 | Medema et al. |
| 6,749,740 B2 | 6/2004 | Liamos et al. |
| 6,752,787 B1 | 6/2004 | Causey, III et al. |
| 6,809,653 B1 | 10/2004 | Mann et al. |
| 6,817,990 B2 | 11/2004 | Yap et al. |
| 6,827,702 B2 | 12/2004 | Lebel et al. |
| 6,881,551 B2 | 4/2005 | Heller et al. |
| 6,892,085 B2 | 5/2005 | McIvor et al. |
| 6,893,545 B2 | 5/2005 | Gotoh et al. |
| 6,895,263 B2 | 5/2005 | Shin et al. |
| 6,916,159 B2 | 7/2005 | Rush et al. |
| 6,932,584 B2 | 8/2005 | Gray et al. |
| 6,932,894 B2 | 8/2005 | Mao et al. |
| 6,942,518 B2 | 9/2005 | Liamos et al. |
| 7,153,263 B2 | 12/2006 | Carter et al. |
| 7,153,289 B2 | 12/2006 | Vasko |
| 7,323,142 B2 | 1/2008 | Pendo et al. |
| 7,396,330 B2 | 7/2008 | Banet et al. |
| 7,402,153 B2 | 7/2008 | Steil et al. |
| 7,404,796 B2 | 7/2008 | Ginsberg |
| 7,621,893 B2 | 11/2009 | Moberg et al. |
| 8,474,332 B2 | 7/2013 | Bente, IV |
| 8,674,288 B2 | 3/2014 | Hanson et al. |
| 2001/0044731 A1 | 11/2001 | Coffman et al. |
| 2002/0002326 A1 | 1/2002 | Causey, III et al. |
| 2002/0013518 A1 | 1/2002 | West et al. |
| 2002/0055857 A1 | 5/2002 | Mault et al. |
| 2002/0082665 A1 | 6/2002 | Haller et al. |
| 2002/0137997 A1 | 9/2002 | Mastrototaro et al. |
| 2002/0161288 A1 | 10/2002 | Shin et al. |
| 2003/0060765 A1 | 3/2003 | Campbell et al. |
| 2003/0078560 A1 | 4/2003 | Miller et al. |
| 2003/0088166 A1 | 5/2003 | Say et al. |
| 2003/0144581 A1 | 7/2003 | Conn et al. |
| 2003/0152823 A1 | 8/2003 | Heller |
| 2003/0176183 A1 | 9/2003 | Drucker et al. |
| 2003/0188427 A1 | 10/2003 | Say et al. |
| 2003/0199744 A1 | 10/2003 | Buse et al. |
| 2003/0208113 A1 | 11/2003 | Mault et al. |
| 2003/0220552 A1 | 11/2003 | Reghabi et al. |
| 2004/0061232 A1 | 4/2004 | Shah et al. |
| 2004/0061234 A1 | 4/2004 | Shah et al. |
| 2004/0064133 A1 | 4/2004 | Miller et al. |
| 2004/0064156 A1 | 4/2004 | Shah et al. |
| 2004/0073095 A1 | 4/2004 | Causey, III et al. |
| 2004/0074785 A1 | 4/2004 | Holker et al. |
| 2004/0093167 A1 | 5/2004 | Braig et al. |
| 2004/0097796 A1 | 5/2004 | Berman et al. |
| 2004/0102683 A1 | 5/2004 | Khanuja et al. |
| 2004/0111017 A1 | 6/2004 | Say et al. |
| 2004/0122353 A1 | 6/2004 | Shahmirian et al. |
| 2004/0167465 A1 | 8/2004 | Mihai et al. |
| 2004/0193025 A1 | 9/2004 | Steil et al. |
| 2004/0263354 A1 | 12/2004 | Mann et al. |
| 2005/0038331 A1 | 2/2005 | Silaski et al. |
| 2005/0038680 A1 | 2/2005 | McMahon et al. |
| 2005/0154271 A1 | 7/2005 | Rasdal et al. |
| 2005/0192557 A1 | 9/2005 | Brauker et al. |
| 2006/0229694 A1 | 10/2006 | Schulman et al. |
| 2006/0238333 A1 | 10/2006 | Welch et al. |
| 2006/0293571 A1 | 12/2006 | Bao et al. |
| 2007/0088521 A1 | 4/2007 | Shmueli et al. |
| 2007/0135866 A1 | 6/2007 | Baker et al. |
| 2008/0154503 A1 | 6/2008 | Wittenber et al. |
| 2008/0206799 A1 | 8/2008 | Blomquist |
| 2008/0234663 A1* | 9/2008 | Yodfat .............. A61M 5/14248 604/890.1 |
| 2009/0081951 A1 | 3/2009 | Erdmann et al. |
| 2009/0082635 A1 | 3/2009 | Baldus et al. |
| 2014/0107607 A1 | 4/2014 | Estes |
| 2014/0128803 A1 | 5/2014 | Dobbles et al. |
| 2015/0057634 A1 | 2/2015 | Mastrototaro et al. |
| 2015/0217051 A1 | 8/2015 | Mastrototaro et al. |
| 2015/0217052 A1 | 8/2015 | Keenan et al. |

FOREIGN PATENT DOCUMENTS

| | | |
|---|---|---|
| EP | 0806738 | 11/1997 |
| EP | 0880936 | 12/1998 |
| EP | 1338295 | 8/2003 |
| EP | 1631036 A2 | 3/2006 |
| GB | 2218831 | 11/1989 |
| WO | WO 96/20745 | 7/1996 |
| WO | WO 96/36389 | 11/1996 |
| WO | WO 96/37246 A1 | 11/1996 |
| WO | WO 97/21456 | 6/1997 |
| WO | WO 98/20439 | 5/1998 |
| WO | WO 98/24358 | 6/1998 |
| WO | WO 98/42407 | 10/1998 |
| WO | WO 98/49659 | 11/1998 |
| WO | WO 98/59487 | 12/1998 |
| WO | WO 99/08183 | 2/1999 |
| WO | WO 99/10801 | 3/1999 |
| WO | WO 99/18532 | 4/1999 |
| WO | WO 99/22236 | 5/1999 |
| WO | WO 00/10628 | 3/2000 |
| WO | WO 00/19887 | 4/2000 |
| WO | WO 00/48112 | 8/2000 |
| WO | WO 02/058537 A2 | 8/2002 |
| WO | WO 03/001329 | 1/2003 |
| WO | WO 03/094090 | 11/2003 |
| WO | WO 2004/093648 A2 | 11/2004 |
| WO | WO 2005/065538 A2 | 7/2005 |
| WO | WO 2009/002455 A1 | 12/2008 |
| WO | WO 2009/086216 A1 | 7/2009 |
| WO | WO 2015/061690 A1 | 4/2015 |

OTHER PUBLICATIONS (Animas Corporation, 1999). Animas . . . bringing new life to insulin therapy.

Bode B W, et al. (1996). Reduction in Severe Hypoglycemia with Long-Term Continuous Subcutaneous Insulin Infusion in Type I Diabetes. Diabetes Care, vol. 19, No. 4, 324-327.

Boland E (1998). Teens Pumping it Up! Insulin Pump Therapy Guide for Adolescents. 2nd Edition.

Brackenridge B P (1992). Carbohydrate Gram Counting A Key to Accurate Mealtime Boluses in Intensive Diabetes Therapy. Practical Diabetology, vol. 11, No. 2, pp. 22-28.

(56) References Cited

OTHER PUBLICATIONS

Brackenridge, B P et al. (1995). Counting Carbohydrates How to Zero in on Good Control. MiniMed Technologies Inc.
Farkas-Hirsch R et al. (1994). Continuous Subcutaneous Insulin Infusion: A Review of the Past and Its Implementation for the Future. Diabetes Spectrum From Research to Practice, vol. 7, No. 2, pp. 80-84, 136-138.
Hirsch I B et al. (1990). Intensive Insulin Therapy for Treatment of Type I Diabetes. Diabetes Care, vol. 13, No. 12, pp. 1265-1283.
Kulkarni K et al. (1999). Carbohydrate Counting a Primer for Insulin Pump Users to Zero in on Good Control. MiniMed Inc.
Marcus A O et al. (1996). Insulin Pump Therapy Acceptable Alternative to Injection Therapy, Postgraduate Medicine, vol. 99, No. 3, pp. 125-142.
Reed J al. (1996). Voice of the Diabetic, vol. 11, No. 3, pp. 1-38.
Skyler J S (1989). Continuous Subcutaneous Insulin Infusion [CSII] With External Devices: Current Status. Update in Drug Delivery Systems, Chapter 13, pp. 163-183. Futura Publishing Company.
Skyler J S et al. (1995). The Insulin Pump Therapy Book Insights from the Experts. MiniMed•Technologies.
Strowig S M (1993). Initiation and Management of Insulin Pump Therapy. The Diabetes Educator, vol. 19, No. 1, pp. 50-60.
Walsh J, et al. (1989). Pumping Insulin: The Art of Using an Insulin Pump. Published by MiniMed• Technologies.
(Intensive Diabetes Management, 1995). Insulin Infusion Pump Therapy. pp. 66-78.
Disetronic My Choice™ D-TRON™ Insulin Pump Reference Manual. (no date).
Disetronic H-TRON® plus Quick Start Manual. (no date).
Disetronic My Choice H-TRONplus Insulin Pump Reference Manual. (no date).
Disetronic H-TRON® plus Reference Manual. (no date).
(MiniMed, 1996). The MiniMed 506. 7 pages. Retrieved on Sep. 16, 2003 from the World Wide Web: http://web.archive.org/web/19961111054527/www.minimed.com/files/506_pic.htm.
(MiniMed, 1997). MiniMed 507 Specifications. 2 pages. Retrieved on Sep. 16, 2003 from the World Wide Web: http://web.archive.org/web/19970124234841/www.minimed.com/files/mmn075.htm.
(MiniMed, 1996). FAQ: The Practical Things . . . pp. 1-4. Retrieved on Sep. 16, 2003 from the World Wide Web: http://web.archive.org/web/19961111054546/www.minimed.com/files/faq_pract.htm.
(MiniMed, 1997). Wanted: a Few Good Belt Clips! 1 page. Retrieved on Sep. 16, 2003 from the World Wide Web: http://web.archive.org/web/19970124234559/www.minimed.com/files/mmn002.htm.
(MiniMed Technologies, 1994). MiniMed 506 Insulin Pump User's Guide.
(MiniMed Technologies, 1994). MiniMed™ Dosage Calculator Initial Meal Bolus Guidelines/MiniMed™ Dosage Calculator Initial Basal Rate Guidelines Percentage Method. 4 pages.
(MiniMed, 1996). MiniMed™ 507 Insulin Pump User's Guide.
(MiniMed, 1997). MiniMed™ 507 Insulin Pump User's Guide.
(MiniMed, 1998). MiniMed 507C Insulin Pump User's Guide.
(MiniMed International, 1998). MiniMed 507C Insulin Pump for those who appreciate the difference.
(MiniMed Inc., 1999). MiniMed 508 Flipchart Guide to Insulin Pump Therapy.
(MiniMed Inc., 1999). Insulin Pump Comparison / Pump Therapy Will Change Your Life.
(MiniMed, 2000). MiniMed® 508 User's Guide.
(MiniMed Inc., 2000). MiniMed® Now [1] Can Meal Bolus Calculator / MiniMed® Now [1] Can Correction Bolus Calculator.
(MiniMed Inc., 2000). Now [1] Can MiniMed Pump Therapy.
(MiniMed Inc., 2000). Now [1] Can MiniMed Diabetes Management.
(Medtronic MiniMed, 2002). The 508 Insulin Pump A Tradition of Excellence.
(Medtronic MiniMed, 2002). Medtronic MiniMed Meal Bolus Calculator and Correction Bolus Calculator. International Version.

Abel, P., et al., "Experience with an implantable glucose sensor as a prerequiste of an artificial beta cell," Biomed. Biochim. Acta 43 (1984) 5, pp. 577-584.
Bindra, Dilbir S., et al., "Design and in Vitro Studies of a Needle-Type Glucose Sensor for a Subcutaneous Monitoring," American Chemistry Society, 1991, 63, pp. 1692-1696.
Boguslavsky, Leonid, et al., "Applications of redox polymers in biosensors," Sold State Ionics 60, 1993, pp. 189-197.
Geise, Robert J., et al., "Electropolymerized 1,3-diaminobenzene for the construction of a 1,1'-dimethylferrocene mediated glucose biosensor," Analytica Chimica Acta, 281, 1993, pp. 467-473.
Gernet, S., et al., "A Planar Glucose Enzyme Electrode," Sensors and Actuators, 17, 1989, pp. 537-540.
Gernet, S., et al., "Fabrication and Characterization of a Planar Electromechanical Cell and its Application as a Glucose Sensor," Sensors and Actuators, 18, 1989, pp. 59-70.
Gorton, L., et al., "Amperometric Biosensors Based on an Apparent Direct Electron Transfer Between Electrodes and Immobilized Peroxiases," Analyst, Aug. 1991, vol. 117, pp. 1235-1241.
Gorton, L., et al., "Amperometric Glucose Sensors Based on Immobilized Glucose-Oxidizing Enymes and Chemically Modified Electrodes," Analytica Chimica Acta, 249, 1991, pp. 43-54.
Gough, D. A., et al., "Two-Dimensional Enzyme Electrode Sensor for Glucose," Analytical Chemistry, vol. 57, No. 5, 1985, pp. 2351-2357.
Gregg, Brian A., et al., "Cross-Linked Redox Gels Containing Glucose Oxidase for Amperometric Biosensor Applications," Analytical Chemistry, 62, pp. 258-263.
Gregg, Brian A., et al., "Redox Polymer Films Containing Enzymes. 1. A Redox-Conducting Epoxy Cement: Synthesis, Characterization, and Electrocatalytic Oxidation of Hydroquinone," The Journal of Physical Chemistry, vol. 95, No. 15, 1991, pp. 5970-5975.
Hashiguchi, Yasuhiro, MD, et al., "Development of a Miniaturized Glucose Monitoring System by Combining a Needle-Type Glucose Sensor With Microdialysis Sampling Method," Diabetes Care, vol. 17, No. 5, May 1994, pp. 387-389.
Heller, Adam, "Electrical Wiring of Redox Enzymes," Acc. Chem. Res., vol. 23, No. 5, May 1990, pp. 128-134.
Jobst, Gerhard, et al., "Thin-Film Microbiosensors for Glucose-Lactate Monitoring," Analytical Chemistry, vol. 68, No. 18, Sep. 15, 1996, pp. 3173-3179.
Johnson, K.W., et al., "In vivo evaluation of an electroenzymatic glucose sensor implanted in subcutaneous tissue," Biosensors & Bioelectronics, 7, 1992, pp. 709-714.
Jönsson, G., et al., "An Electromechanical Sensor for Hydrogen Peroxide Based on Peroxidase Adsorbed on a Spectrographic Graphite Electrode," Electroanalysis, 1989, pp. 465-468.
Kanapieniene, J. J., et al., "Miniature Glucose Biosensor with Extended Linearity," Sensors and Actuators, B. 10, 1992, pp. 37-40.
Kawamori, Ryuzo, et al., "Perfect Normalization of Excessive Glucagon Responses to Intravenous Arginine in Human Diabetes Mellitus With the Artificial Beta-Cell," Diabetes vol. 29, Sep. 1980, pp. 762-765.
Kimura, J., et al., "An Immobilized Enzyme Membrane Fabrication Method," Biosensors 4, 1988, pp. 41-52.
Koudelka, M., et al., "In-vivo Behaviour of Hypodermically Implanted Microfabricated Glucose Sensors," Biosensors & Bioelectronics 6, 1991, pp. 31-36.
Koudelka, M., et al., "Planar Amperometric Enzyme-Based Glucose Microelectrode," Sensors & Actuators, 18, 1989, pp. 157-165.
Mastrototaro, John J., et al., "An electroenzymatic glucose sensor fabricated on a flexible substrate," Sensors & Actuators, B. 5, 1991, pp. 139-144.
Mastrototaro, John J., et al., "An Electroenzymatic Sensor Capable of 72 Hour Continuous Monitoring of Subcutaneous Glucose," 14th Annual International Diabetes Federation Congress, Washington D.C., Jun. 23-28, 1991.
McKean, Brian D., et al., "A Telemetry-Instrumentation System for Chronically Implanted Glucose and Oxygen Sensors," IEEE Transactions on Biomedical Engineering, Vo. 35, No. 7, Jul. 1988, pp. 526-532.
Monroe, D., "Novel Implantable Glucose Sensors," ACL, Dec. 1989, pp. 8-16.

(56) References Cited

OTHER PUBLICATIONS

Morff, Robert J., et al., "Microfabrication of Reproducible, Economical, Electroenzymatic Glucose Sensors," Annuaal International Conference of teh IEEE Engineering in Medicine and Biology Society, Vo. 12, No. 2, 1990, pp. 483-484.
Moussy, Francis, et al., "Performance of Subcutaneously Implanted Needle-Type Glucose Sensors Employing a Novel Trilayer Coating," Analytical Chemistry, vol. 65, No. 15, Aug. 1, 1993, pp. 2072-2077.
Nakamoto, S., et al., "A Lift-Off Method for Patterning Enzyme-Immobilized Membranes in Multi-Biosensors," Sensors and Actuators 13, 1988, pp. 165-172.
Nishida, Kenro, et al., "Clinical applications of teh wearable artifical endocrine pancreas with the newly designed needle-type glucose sensor," Elsevier Sciences B.V., 1994, pp. 353-358.
Nishida, Kenro, et al., "Development of a ferrocene-mediated needle-type glucose sensor covereed with newly designd biocompatible membrane, 2-methacryloyloxyethylphosphorylcholine -co-n-butyl nethacrylate," Medical Progress Through Technology, vol. 21, 1995, pp. 91-103.
Poitout, V., et al., "A glucose monitoring system for on line estimation oin man of blood glucose concentration using a miniaturized glucose sensor implanted in the subcutaneous tissue adn a wearable control unit," Diabetologia, vol. 36, 1991, pp. 658-663.
Reach, G., "A Method for Evaluating in vivo the Functional Characteristics of Glucose Sensors," Biosensors 2, 1986, pp. 211-220.
Shaw, G. W., et al., "In vitro testing of a simply constructed, highly stable glucose sensor suitable for implantation in diabetic patients," Biosensors & Bioelectronics 6, 1991, pp. 401-406.
Shichiri, M., "A Needle-Type Glucose Sensor—A Valuable Tool Not Only for a Self-Blood Glucose Monitoring but for a Wearable Artifiical Pancreas," Life Support Systems Proceedings, XI Annual Meeting ESAO, Alpbach-Innsbruck, Austria, Sep. 1984, pp. 7-9.
Shichiri, Motoaki, et al., "An artificial endocrine pancreas—problems awaiting solution for long-term clinical applications of a glucose sensor," Frontiers Med. Biol. Engng., 1991, vol. 3, No. 4, pp. 283-292.
Shichiri, Motoaki, et al., "Closed-Loop Glycemic Control with a Wearable Artificial Endocrine Pancreas—Variations in Daily Insulin Requirements to Glycemic Response," Diabetes, vol. 33, Dec. 1984, pp. 1200-1202.
Shichiri, Motoaki, et al., "Glycaemic Control in a Pacreatectomized Dogs with a Wearable Artificial Endocrine Pancreas," Diabetologia, vol. 24, 1983, pp. 179-184.
Shichiri, M., et al., "In Vivo Characteristics of Needle-Type Glucose Sensor—Measurements of Subcutaneous Glucose Concentrations in Human Volunteers," Hormone and Metabolic Research, Supplement Series vol. No. 20, 1988, pp. 17-20.
Shichiri, M., et al., "Membrane design for extending the long-life of an implantable glucose sensor," Diab. Nutr. Metab., vol. 2, No. 4, 1989, pp. 309-313.
Shichiri, Motoaki, et al., "Normalization of the Paradoxic Secretion of Glucagon in Diabetes Who Were Controlled by the Artificial Beta Cell," Diabetes, vol. 28, Apr. 1979, pp. 272-275.
Shichiri, Motoaki, et al., "Telemetry Glucose Monitoring Device with Needle-Type Glucose Sensor: A useful Tool for Blood Glucose Monitoring in Diabetic Individuals," Diabetes Care, vol. 9, No. 3, May-Jun. 1986, pp. 298-301.
Shichiri, Motoaki, et al., "Wearable Artificial Endocrine Pancreas with Needle-Type Glucose Sensor," The Lancet, Nov. 20, 1982, pp. 1129-1131.
Shichiri, Motoaki, et al., "The Wearable Artificial Endocrine Pancreas with a Needle-Type Glucose Sensor: Perfect Glycemic Control in Ambulatory Diabetes," Acta Paediatr Jpn 1984, vol. 26, pp. 359-370.
Shinkai, Seiji, "Molecular Recognitiion of Mono- and Di-saccharides by Phenylboronic Acids in Solvent Extraction and as a Monolayer," J. Chem. Soc., Chem. Commun., 1991, pp. 1039-1041.
Shults, Mark C., "A Telemetry-Instrumentation System for Monitoring Multiple Subcutaneously Implanted Glucose Sensors," IEEE Transactions on Biomedical Engineering, vol. 41, No. 10, Oct. 1994, pp. 937-942.
Sternberg, Robert, et al., "Study and Development of Multilayer Needle-type Enzyme-based Glucose Microsensors," Biosensors, vol. 4, 1988, pp. 27-40.
Tamiya, E., et al., "Micro Glucose Sensors using Electron Mediators Immobilized on a Polypyrrole-Modified Electrode," Sensors and Actuators, vol. 18, 1989, pp. 297-307.
Tsukagoshi, Kazuhiko, et al., "Specific Complexation with Mono- and Disaccharides that can be Detected by Circular Dichroism," J. Org. Chem., vol. 56, 1991, pp. 4089-4091.
Urban, G., et al., "Miniaturized multi-enzyme biosensors integrated with pH sensors on flexible polymer carriers for in vivo applciations," Biosensors & Bioelectronics, vol. 7, 1992, pp. 733-739.
Ubran, G., et al., "Miniaturized thin-film biosensors using covalently immobilized glucose oxidase," Biosensors & Bioelectronics, vol. 6, 1991, pp. 555-562.
Velho, G., et al., "In vivo calibration of a subcutaneous glucose sensor for determination of subcutaneous glucose kinetics," Diab. Nutr. Metab., vol. 3, 1988, pp. 227-233.
Wang, Joseph, et al., "Needle-Type Dual Microsensor for the Simultaneous Monitoring of Glucose and Insulin," Analytical Chemistry, vol. 73, 2001, pp. 844-847.
Yamasaki, Yoshimitsu, et al., "Direct Measurement of Whole Blood Glucose by a Needle-Type Sensor," Clinics Chimica Acta, vol. 93, 1989, pp. 93-98.
Yokoyama, K., "Integrated Biosensor for Glucose and Galactose," Analytica Chimica Acta, vol. 218, 1989, pp. 137-142.

\* cited by examiner

INFUSION DEVICES AND RELATED PATIENT RATIO ADJUSTMENT METHODS

CROSS-REFERENCE TO RELATED APPLICATION(S)

This application claims the benefit of U.S. provisional patent application Ser. No. 62/208,454, filed Aug. 21, 2015, the entire content of which is incorporated by referenhce herein.

TECHNICAL FIELD

Embodiments of the subject matter described herein relate generally to medical devices, and more particularly, embodiments of the subject matter relate to providing dynamic and adaptive adjustments to patient-specific control ratios during operation of a fluid infusion device.

BACKGROUND

Infusion pump devices and systems are relatively well known in the medical arts, for use in delivering or dispensing an agent, such as insulin or another prescribed medication, to a patient. A typical infusion pump includes a pump drive system which typically includes a small motor and drive train components that convert rotational motor motion to a translational displacement of a plunger (or stopper) in a reservoir that delivers medication from the reservoir to the body of a user via a fluid path created between the reservoir and the body of a user. Use of infusion pump therapy has been increasing, especially for delivering insulin for diabetics.

While control schemes may allow insulin infusion pumps to monitor and regulate a user's blood glucose level in a substantially continuous and autonomous manner, it is common to manually initiate delivery of insulin prior to or contemporaneously with consuming a meal (e.g., a meal bolus or correction bolus) to prevent spikes or swings in the user's blood glucose level that could otherwise result from the impending consumption of carbohydrates and the response time of the control scheme. However, regulating blood glucose level is complicated by variations in the response time for the type of insulin being used along with variations in a user's individual insulin response and daily activities (e.g., exercise, carbohydrate consumption, bolus administration, and the like). Additionally, the patient-specific ratios, factors, or other control parameters used to determine the bolus amount can vary depending on the particular techniques or preferences used by the individual making the determination. Thus, the efficacy of the manual boluses can vary on a user-by-user basis, but also throughout the day for an individual user based on variations in the user's daily activities. Accordingly, there is a need to improve the efficacy of manual boluses and minimize postprandial glucose excursions.

BRIEF SUMMARY

Infusion systems, infusion devices, and related operating methods are provided. An embodiment of a method of operating an infusion device to deliver fluid to a body of a user is provided. The method involves identifying a residual value for a physiological condition in the body of the user based on measurement values for the physiological condition in the body of the user, where the residual value resulted from a bolus amount of the fluid delivered by the infusion device, and where the bolus amount was influenced by an initial ratio associated with the user and stored in a data storage element onboard the infusion device. The method continues by determining an updated ratio by adjusting the initial ratio to compensate for the residual value and storing the updated ratio in the data storage element, wherein a subsequent bolus amount is influenced by the updated ratio.

An embodiment of an infusion device is also provided. The infusion device includes an actuation arrangement operable to deliver fluid to a body of a user, a data storage element, a communications interface to receive measurement values indicative of a physiological condition in the body of the user that is influenced by the fluid, and a control module coupled to the actuation arrangement, the data storage element, and the communications interface. The control module operates the actuation arrangement to deliver a bolus amount of the fluid influenced by an initial value for a ratio stored by the data storage element, identifies a residual value for the physiological condition based at least in part on one or more of the measurement values after delivery of the bolus amount, determines an updated value for the ratio by adjusting the initial value to compensate for the residual value, and stores the updated value for the ratio in the data storage element.

In another embodiment, a method of operating an infusion device to deliver insulin to a user is provided. The method involves a control module of the infusion device determining a bolus amount of insulin based on an input carbohydrate amount and a value for a carbohydrate ratio stored onboard the infusion device, identifying a residual glucose value based on glucose measurement values after delivery of the bolus amount of insulin, determining an adjustment factor for the carbohydrate ratio based on the residual glucose value, and scaling the value by the adjustment factor to obtain an updated value for the carbohydrate ratio. The method continues with the control module storing the updated value for the carbohydrate ratio onboard the infusion device and thereafter determining a second bolus amount of insulin based on a second input carbohydrate amount and the updated value for the carbohydrate ratio stored onboard the infusion device.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures, which may be illustrated for simplicity and clarity and are not necessarily drawn to scale.

DETAILED DESCRIPTION

Figure 1:
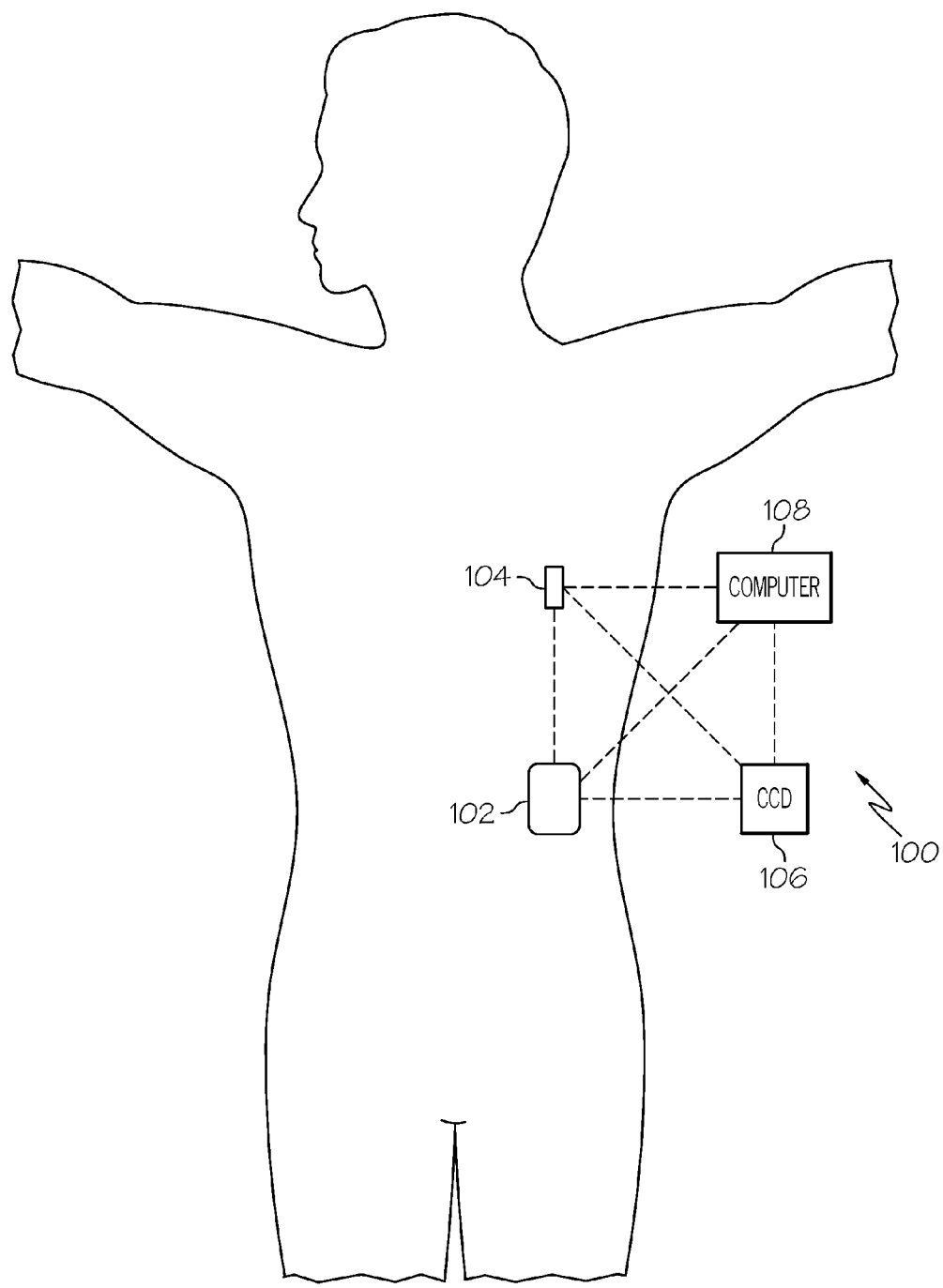
FIG. 1 depicts an exemplary embodiment of an infusion system.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

While the subject matter described herein can be implemented in any electronic device that includes a motor, exemplary embodiments described below are implemented in the form of medical devices, such as portable electronic medical devices. Although many different applications are possible, the following description focuses on a fluid infusion device (or infusion pump) as part of an infusion system deployment. For the sake of brevity, conventional techniques related to infusion system operation, insulin pump and/or infusion set operation, and other functional aspects of the systems (and the individual operating components of the systems) may not be described in detail here. Examples of infusion pumps may be of the type described in, but not limited to, U.S. Pat. Nos. 4,562,751; 4,685,903; 5,080,653; 5,505,709; 5,097,122; 6,485,465; 6,554,798; 6,558,320; 6,558,351; 6,641,533; 6,659,980; 6,752,787; 6,817,990; 6,932,584; and 7,621,893; each of which are herein incorporated by reference.

Embodiments of the subject matter described herein generally relate to fluid infusion devices including a motor or other actuation arrangement that is operable to linearly displace a plunger (or stopper) of a reservoir provided within the fluid infusion device to deliver a dosage of fluid, such as insulin, to the body of a user. Dosage commands that govern operation of the motor may be generated in an automated manner in accordance with the delivery control scheme associated with a particular operating mode, and the dosage commands may be generated in a manner that is influenced by a current (or most recent) measurement of a physiological condition in the body of the user. For example, in a closed-loop operating mode, dosage commands may be generated based on a difference between a current (or most recent) measurement of the interstitial fluid glucose level in the body of the user and a target (or reference) glucose value. In this regard, the rate of infusion may vary as the difference between a current measurement value and the target measurement value fluctuates. For purposes of explanation, the subject matter is described herein in the context of the infused fluid being insulin for regulating a glucose level of a user (or patient); however, it should be appreciated that many other fluids may be administered through infusion, and the subject matter described herein is not necessarily limited to use with insulin.

Often a user (or patient) manually operates an infusion device to deliver a bolus of insulin at mealtime (often referred to as a "meal bolus" or "correction bolus"), which is intended to compensate for or otherwise mitigate a potential spike in the user's glucose level attributable to the amount of carbohydrates consumed during the meal. The user manually inputs the amount of carbohydrates being consumed, which, in turn are converted to a corresponding amount of insulin units using a carbohydrate conversion ratio, which may be maintained by the infusion device. The carbohydrate conversion ratio can be specific to that individual, and can be determined by the user or the user's care provider using any of a number of potential techniques or methodologies before being stored onboard the infusion device for use in subsequently administering meal boluses.

As described in greater detail below, primarily in the context of FIGS. 7-10, in exemplary embodiments described herein, measurements of a user's glucose level are monitored and analyzed after a bolus of insulin is delivered, and based on the user's glucose measurements, a residual value representing a deviation from the user's pre-bolus and pre-meal glucose level after metabolization of the bolus and the meal is identified. In this regard, the residual glucose value represents an amount, in terms of the user's glucose level, that the bolus overcompensated or undercompensated for the amount of carbohydrates consumed by the user during the meal, that is, the difference between the user's post-prandial glucose settling value and the user's pre-prandial glucose value. Using the residual glucose value, the user's carbohydrate ratio is adjusted to compensate for the residual value. For example, when the residual glucose value is positive and thereby indicative of an insufficient bolus amount, the user's carbohydrate ratio is updated to a lower value configured to increase subsequent meal bolus amounts (on a per carbohydrate unit basis). Conversely, when the residual glucose value is negative and thereby indicative of an excessive bolus amount, the user's carbohydrate ratio is updated to a higher value configured to decrease subsequent meal bolus amounts (on a per carbohydrate unit basis).

By virtue of the carbohydrate ratio being adaptively adjusted to compensate for the residual glucose level, subsequent meal boluses may more effectively compensate for consumed carbohydrates and mitigate glucose excursions attributable to meal consumption, over time resulting in a post-prandial glucose level substantially equal to the pre-prandial glucose level as the carbohydrate ratio converges towards a stable value. Some embodiments may employ different context-sensitive patient-specific carbohydrate ratios associated with different times of the day, different days of the week, or other different bolus contexts, with those context-sensitive patient-specific carbohydrate ratios also being adaptively and dynamically adjusted based on boluses having the same context, which, in turn, may further improve the effectiveness of meal boluses associated with the same bolus context (e.g., time of day, day of week, etc.).

Figure 9:
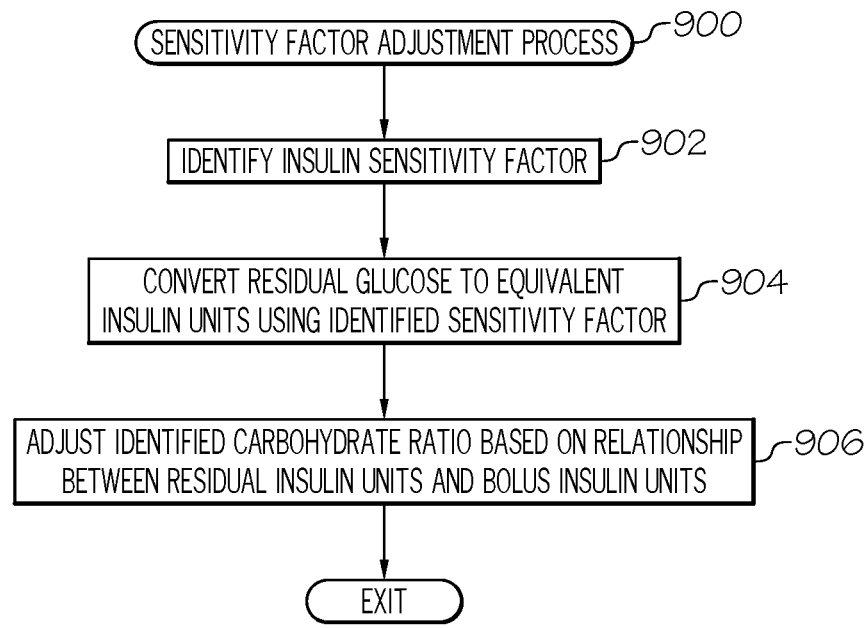
FIG. 9 is a flow diagram of an exemplary sensitivity factor adjustment process suitable for use with the adaptive ratio adjustment process of FIG. 7 in one or more exemplary embodiments.

As described in the context of FIG. 9, in one or more embodiments, the user's carbohydrate ratio is scaled by an adjustment factor corresponding to the ratio of the delivered meal bolus amount to the sum of the delivered meal bolus amount and a residual amount of insulin corresponding to the residual glucose value. In such embodiments, the residual glucose value is converted to a corresponding residual amount of units of insulin using the user's insulin sensitivity factor, with the residual insulin amount then being used to increase or decrease the carbohydrate ratio inversely to the magnitude of the residual insulin amount (e.g., a negative residual insulin amount increases the carbohydrate ratio and a positive residual insulin amount decreases the carbohydrate ratio).

Figure 10:
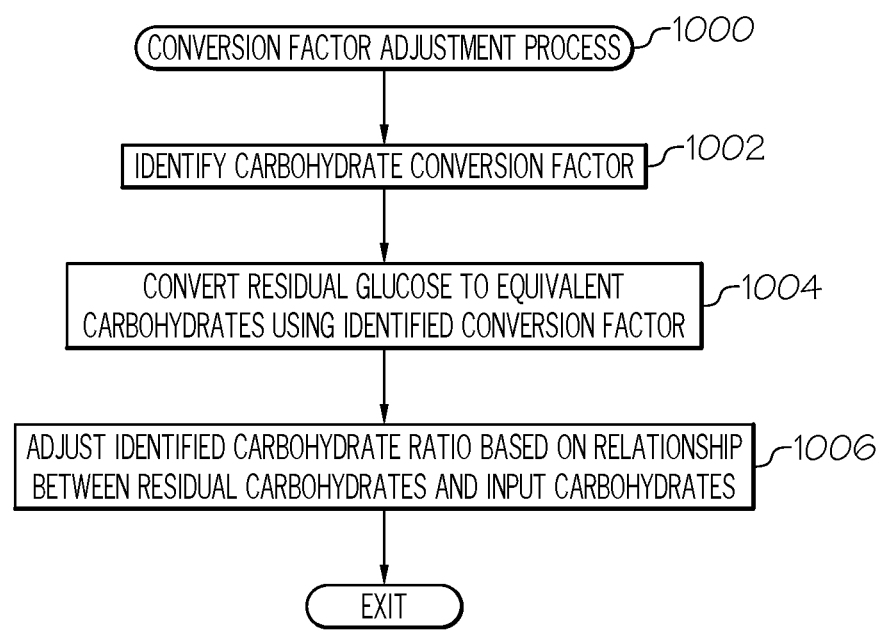
FIG. 10 is a flow diagram of an exemplary conversion factor adjustment process suitable for use with the adaptive ratio adjustment process of FIG. 7 in one or more exemplary embodiments.

In other embodiments described in the context of FIG. 10, the user's carbohydrate ratio is scaled by an adjustment factor corresponding to the ratio of a difference between the input meal carbohydrate amount and a residual carbohydrate amount relative to the input meal carbohydrate amount. In such embodiments, the residual glucose value is converted to a corresponding residual amount of carbohydrates for which the delivered bolus overcompensated (in the case of a negative value) or undercompensated for (in the case of a positive value) of insulin using the user's insulin sensitivity factor. The residual carbohydrate amount is then used to increase or decrease the carbohydrate ratio inversely to the magnitude of the residual insulin carbohydrate (e.g., a negative residual carbohydrate amount increases the carbohydrate ratio and a positive residual insulin amount decreases the carbohydrate ratio).

Turning now to FIG. 1, one exemplary embodiment of an infusion system 100 includes, without limitation, a fluid infusion device (or infusion pump) 102, a sensing arrangement 104, a command control device (CCD) 106, and a computer 108. The components of an infusion system 100 may be realized using different platforms, designs, and configurations, and the embodiment shown in FIG. 1 is not exhaustive or limiting. In practice, the infusion device 102 and the sensing arrangement 104 are secured at desired locations on the body of a user (or patient), as illustrated in FIG. 1. In this regard, the locations at which the infusion device 102 and the sensing arrangement 104 are secured to the body of the user in FIG. 1 are provided only as a representative, non-limiting, example. The elements of the infusion system 100 may be similar to those described in U.S. Pat. No. 8,674,288, the subject matter of which is hereby incorporated by reference in its entirety.

In the illustrated embodiment of FIG. 1, the infusion device 102 is designed as a portable medical device suitable for infusing a fluid, a liquid, a gel, or other agent into the body of a user. In exemplary embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. In some embodiments, the fluid may include a nutritional supplement, a dye, a tracing medium, a saline medium, a hydration medium, or the like.

The sensing arrangement 104 generally represents the components of the infusion system 100 configured to sense, detect, measure or otherwise quantify a condition of the user, and may include a sensor, a monitor, or the like, for providing data indicative of the condition that is sensed, detected, measured or otherwise monitored by the sensing arrangement. In this regard, the sensing arrangement 104 may include electronics and enzymes reactive to a biological or physiological condition of the user, such as a blood glucose level, or the like, and provide data indicative of the blood glucose level to the infusion device 102, the CCD 106 and/or the computer 108. For example, the infusion device 102, the CCD 106 and/or the computer 108 may include a display for presenting information or data to the user based on the sensor data received from the sensing arrangement 104, such as, for example, a current glucose level of the user, a graph or chart of the user's glucose level versus time, device status indicators, alert messages, or the like. In other embodiments, the infusion device 102, the CCD 106 and/or the computer 108 may include electronics and software that are configured to analyze sensor data and operate the infusion device 102 to deliver fluid to the body of the user based on the sensor data and/or preprogrammed delivery routines. Thus, in exemplary embodiments, one or more of the infusion device 102, the sensing arrangement 104, the CCD 106, and/or the computer 108 includes a transmitter, a receiver, and/or other transceiver electronics that allow for communication with other components of the infusion system 100, so that the sensing arrangement 104 may transmit sensor data or monitor data to one or more of the infusion device 102, the CCD 106 and/or the computer 108.

Still referring to FIG. 1, in various embodiments, the sensing arrangement 104 may be secured to the body of the user or embedded in the body of the user at a location that is remote from the location at which the infusion device 102 is secured to the body of the user. In various other embodiments, the sensing arrangement 104 may be incorporated within the infusion device 102. In other embodiments, the sensing arrangement 104 may be separate and apart from the infusion device 102, and may be, for example, part of the CCD 106. In such embodiments, the sensing arrangement 104 may be configured to receive a biological sample, analyte, or the like, to measure a condition of the user.

In various embodiments, the CCD 106 and/or the computer 108 may include electronics and other components configured to perform processing, delivery routine storage, and to control the infusion device 102 in a manner that is influenced by sensor data measured by and/or received from the sensing arrangement 104. By including control functions in the CCD 106 and/or the computer 108, the infusion device 102 may be made with more simplified electronics. However, in other embodiments, the infusion device 102 may include all control functions, and may operate without the CCD 106 and/or the computer 108. In various embodiments, the CCD 106 may be a portable electronic device. In addition, in various embodiments, the infusion device 102 and/or the sensing arrangement 104 may be configured to transmit data to the CCD 106 and/or the computer 108 for display or processing of the data by the CCD 106 and/or the computer 108.

In some embodiments, the CCD 106 and/or the computer 108 may provide information to the user that facilitates the user's subsequent use of the infusion device 102. For example, the CCD 106 may provide information to the user to allow the user to determine the rate or dose of medication to be administered into the user's body. In other embodiments, the CCD 106 may provide information to the infusion device 102 to autonomously control the rate or dose of medication administered into the body of the user. In some embodiments, the sensing arrangement 104 may be integrated into the CCD 106. Such embodiments may allow the user to monitor a condition by providing, for example, a sample of his or her blood to the sensing arrangement 104 to assess his or her condition. In some embodiments, the sensing arrangement 104 and the CCD 106 may be used for determining glucose levels in the blood and/or body fluids of the user without the use of, or necessity of, a wire or cable connection between the infusion device 102 and the sensing arrangement 104 and/or the CCD 106.

In one or more exemplary embodiments, the sensing arrangement 104 and/or the infusion device 102 are cooperatively configured to utilize a closed-loop system for delivering fluid to the user. Examples of sensing devices and/or infusion pumps utilizing closed-loop systems may be found at, but are not limited to, the following U.S. Pat. Nos. 6,088,608, 6,119,028, 6,589,229, 6,740,072, 6,827,702, 7,323,142, and 7,402,153, all of which are incorporated herein by reference in their entirety. In such embodiments, the sensing arrangement 104 is configured to sense or measure a condition of the user, such as, blood glucose level or the like. The infusion device 102 is configured to deliver fluid in response to the condition sensed by the sensing arrangement 104. In turn, the sensing arrangement 104 continues to sense or otherwise quantify a current condition of the user, thereby allowing the infusion device 102 to deliver fluid continuously in response to the condition currently (or most recently) sensed by the sensing arrangement 104 indefinitely. In some embodiments, the sensing arrangement 104 and/or the infusion device 102 may be configured to utilize the closed-loop system only for a portion of the day, for example only when the user is asleep or awake.

Figure 2:
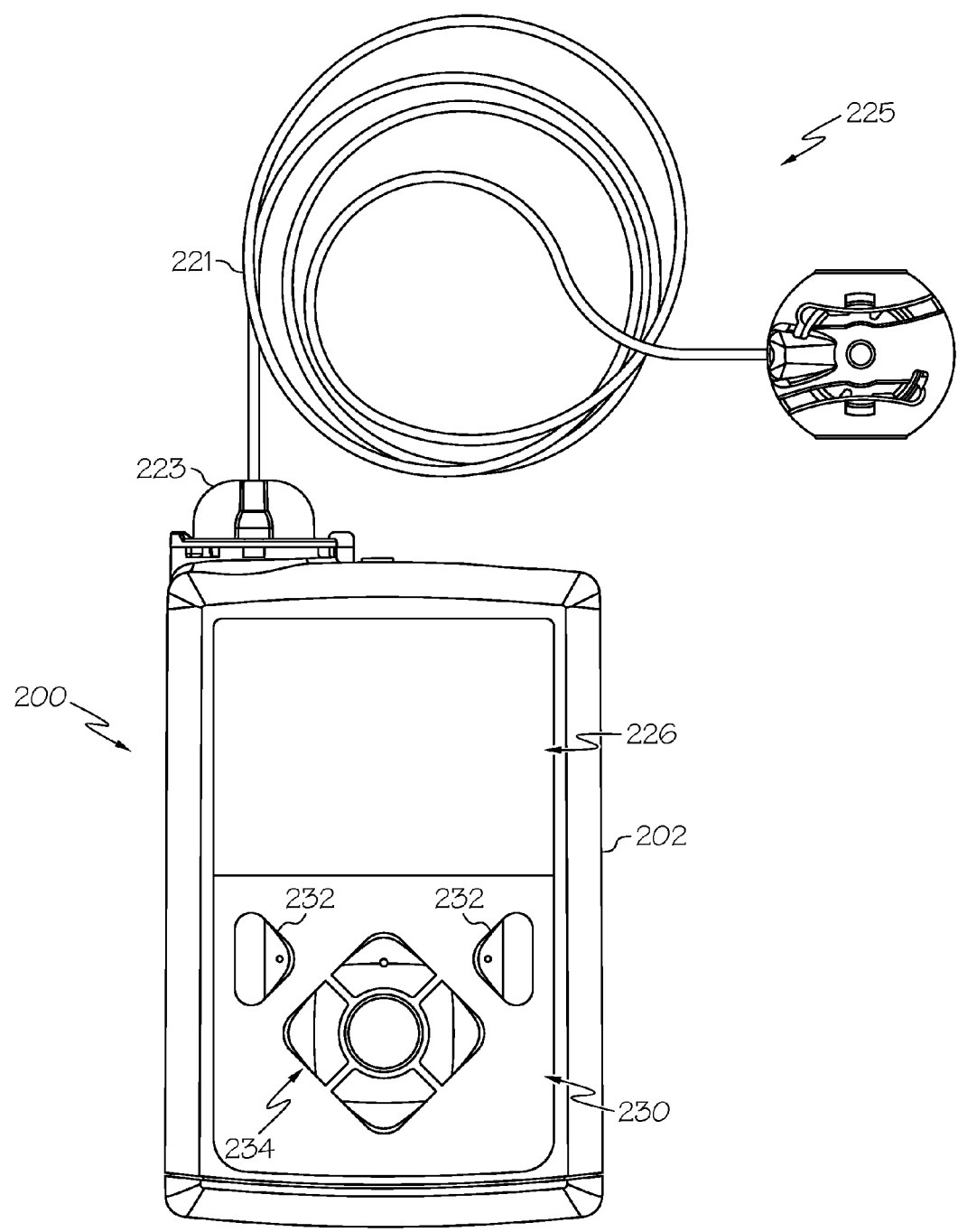
FIG. 2 depicts a plan view of an exemplary embodiment of a fluid infusion device suitable for use in the infusion system of FIG. 1.
Figure 3:
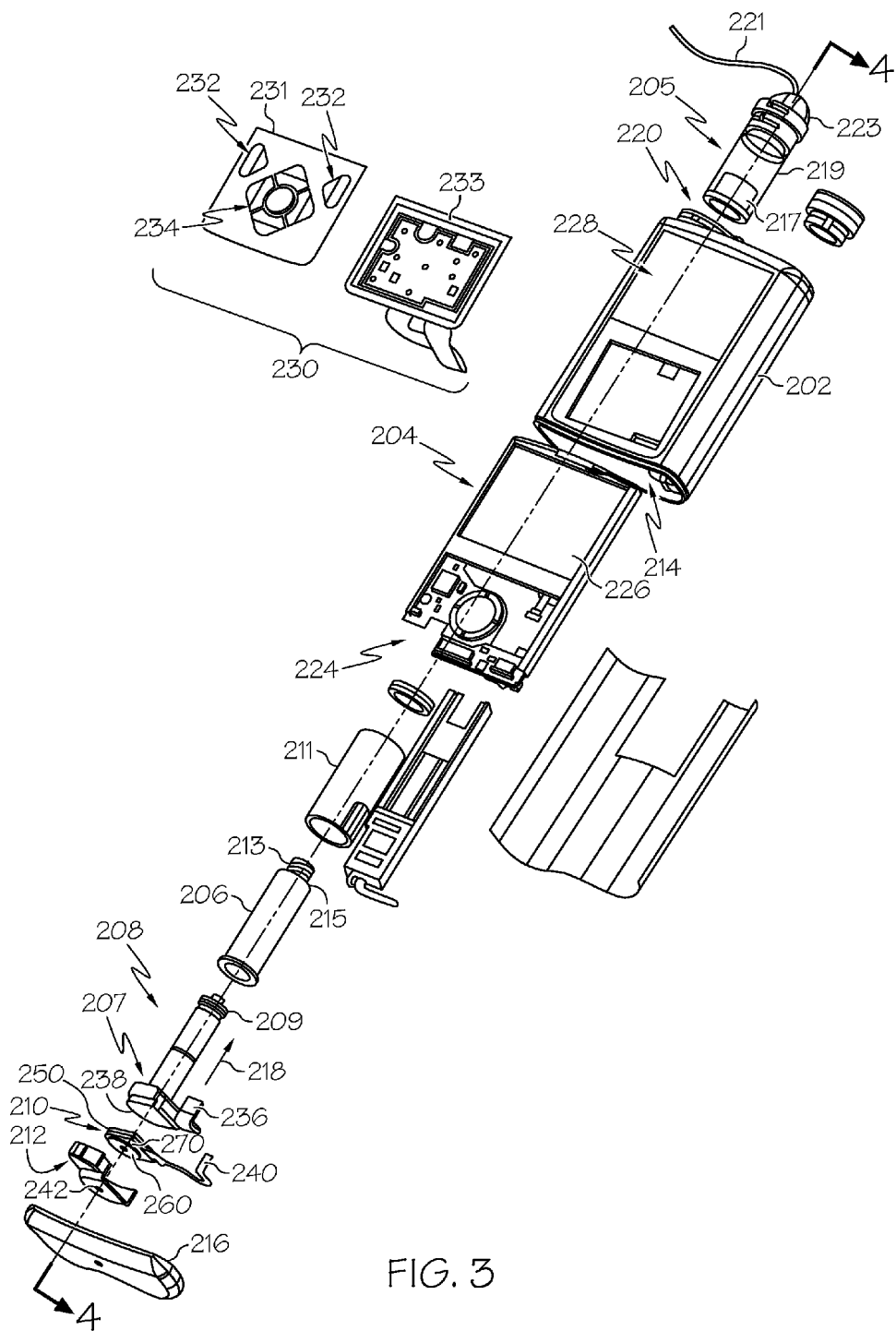
FIG. 3 is an exploded perspective view of the fluid infusion device of FIG. 2.
Figure 4:
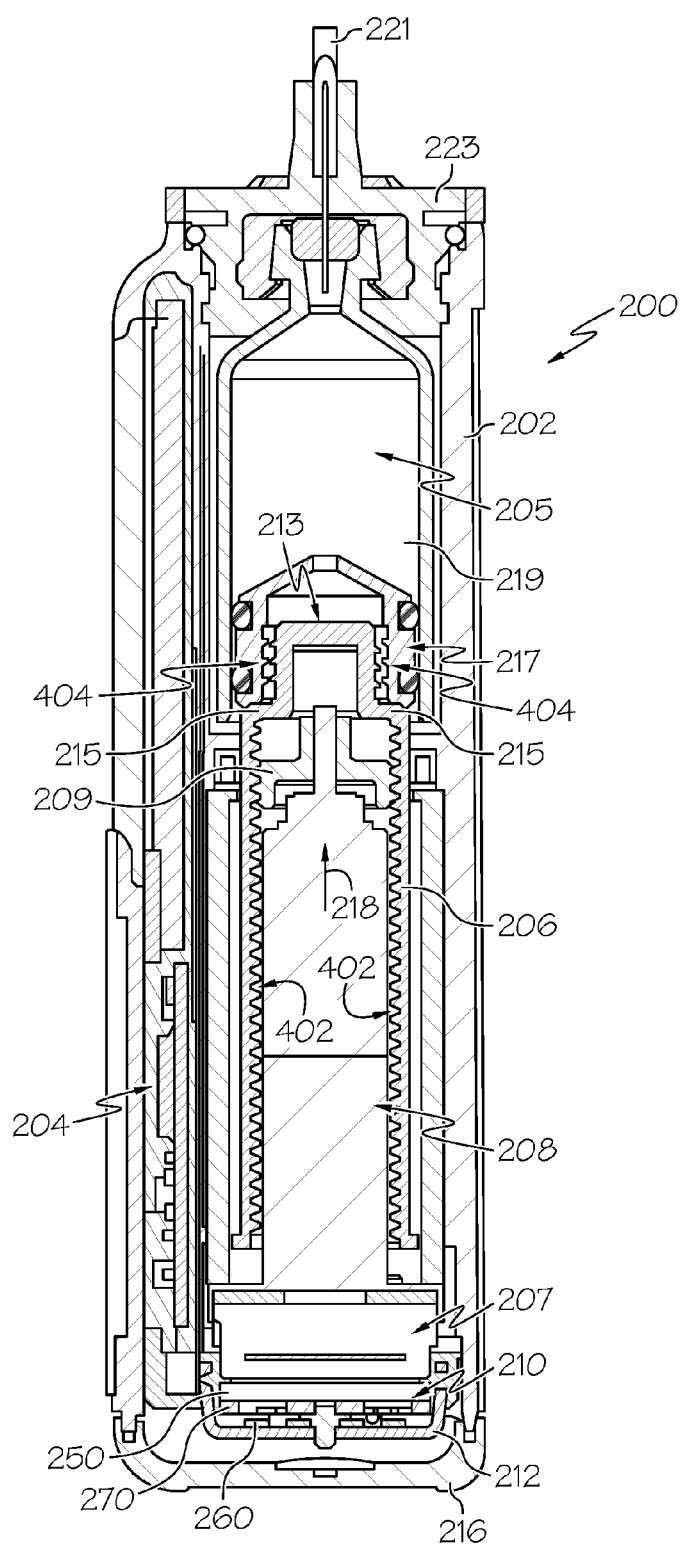
FIG. 4 is a cross-sectional view of the fluid infusion device of FIGS. 2-3 as viewed along line 4-4 in FIG. 3 when assembled with a reservoir inserted in the infusion device.

FIGS. 2-4 depict one exemplary embodiment of a fluid infusion device 200 (or alternatively, infusion pump) suitable for use in an infusion system, such as, for example, as infusion device 102 in the infusion system 100 of FIG. 1. The fluid infusion device 200 is a portable medical device designed to be carried or worn by a patient (or user), and the fluid infusion device 200 may leverage any number of conventional features, components, elements, and characteristics of existing fluid infusion devices, such as, for example, some of the features, components, elements, and/or characteristics described in U.S. Pat. Nos. 6,485,465 and 7,621,893. It should be appreciated that FIGS. 2-4 depict some aspects of the infusion device 200 in a simplified manner; in practice, the infusion device 200 could include additional elements, features, or components that are not shown or described in detail herein.

As best illustrated in FIGS. 2-3, the illustrated embodiment of the fluid infusion device 200 includes a housing 202 adapted to receive a fluid-containing reservoir 205. An opening 220 in the housing 202 accommodates a fitting 223 (or cap) for the reservoir 205, with the fitting 223 being configured to mate or otherwise interface with tubing 221 of an infusion set 225 that provides a fluid path to/from the body of the user. In this manner, fluid communication from the interior of the reservoir 205 to the user is established via the tubing 221. The illustrated fluid infusion device 200 includes a human-machine interface (HMI) 230 (or user interface) that includes elements 232, 234 that can be manipulated by the user to administer a bolus of fluid (e.g., insulin), to change therapy settings, to change user preferences, to select display features, and the like. The infusion device also includes a display element 226, such as a liquid crystal display (LCD) or another suitable display element, that can be used to present various types of information or data to the user, such as, without limitation: the current glucose level of the patient; the time; a graph or chart of the patient's glucose level versus time; device status indicators; etc.

The housing 202 is formed from a substantially rigid material having a hollow interior 214 adapted to allow an electronics assembly 204, a sliding member (or slide) 206, a drive system 208, a sensor assembly 210, and a drive system capping member 212 to be disposed therein in addition to the reservoir 205, with the contents of the housing 202 being enclosed by a housing capping member 216. The opening 220, the slide 206, and the drive system 208 are coaxially aligned in an axial direction (indicated by arrow 218), whereby the drive system 208 facilitates linear displacement of the slide 206 in the axial direction 218 to dispense fluid from the reservoir 205 (after the reservoir 205 has been inserted into opening 220), with the sensor assembly 210 being configured to measure axial forces (e.g., forces aligned with the axial direction 218) exerted on the sensor assembly 210 responsive to operating the drive system 208 to displace the slide 206. In various embodiments, the sensor assembly 210 may be utilized to detect one or more of the following: an occlusion in a fluid path that slows, prevents, or otherwise degrades fluid delivery from the reservoir 205 to a user's body; when the reservoir 205 is empty; when the slide 206 is properly seated with the reservoir 205; when a fluid dose has been delivered; when the infusion pump 200 is subjected to shock or vibration; when the infusion pump 200 requires maintenance.

Depending on the embodiment, the fluid-containing reservoir 205 may be realized as a syringe, a vial, a cartridge, a bag, or the like. In certain embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. As best illustrated in FIGS. 3-4, the reservoir 205 typically includes a reservoir barrel 219 that contains the fluid and is concentrically and/or coaxially aligned with the slide 206 (e.g., in the axial direction 218) when the reservoir 205 is inserted into the infusion pump 200. The end of the reservoir 205 proximate the opening 220 may include or otherwise mate with the fitting 223, which secures the reservoir 205 in the housing 202 and prevents displacement of the reservoir 205 in the axial direction 218 with respect to the housing 202 after the reservoir 205 is inserted into the housing 202. As described above, the fitting 223 extends from (or through) the opening 220 of the housing 202 and mates with tubing 221 to establish fluid communication from the interior of the reservoir 205 (e.g., reservoir barrel 219) to the user via the tubing 221 and infusion set 225. The opposing end of the reservoir 205 proximate the slide 206 includes a plunger 217 (or stopper) positioned to push fluid from inside the barrel 219 of the reservoir 205 along a fluid path through tubing 221 to a user. The slide 206 is configured to mechanically couple or otherwise engage with the plunger 217, thereby becoming seated with the plunger 217 and/or reservoir 205. Fluid is forced from the reservoir 205 via tubing 221 as the drive system 208 is operated to displace the slide 206 in the axial direction 218 toward the opening 220 in the housing 202.

In the illustrated embodiment of FIGS. 3-4, the drive system 208 includes a motor assembly 207 and a drive screw 209. The motor assembly 207 includes a motor that is coupled to drive train components of the drive system 208 that are configured to convert rotational motor motion to a translational displacement of the slide 206 in the axial direction 218, and thereby engaging and displacing the plunger 217 of the reservoir 205 in the axial direction 218. In some embodiments, the motor assembly 207 may also be powered to translate the slide 206 in the opposing direction (e.g., the direction opposite direction 218) to retract and/or detach from the reservoir 205 to allow the reservoir 205 to be replaced. In exemplary embodiments, the motor assembly 207 includes a brushless DC (BLDC) motor having one or more permanent magnets mounted, affixed, or otherwise disposed on its rotor. However, the subject matter described herein is not necessarily limited to use with BLDC motors, and in alternative embodiments, the motor may be realized as a solenoid motor, an AC motor, a stepper motor, a piezoelectric caterpillar drive, a shape memory actuator drive, an electrochemical gas cell, a thermally driven gas cell, a bimetallic actuator, or the like. The drive train components may comprise one or more lead screws, cams, ratchets, jacks, pulleys, pawls, clamps, gears, nuts, slides, bearings, levers, beams, stoppers, plungers, sliders, brackets, guides, bearings, supports, bellows, caps, diaphragms, bags, heaters, or the like. In this regard, although the illustrated embodiment of the infusion pump utilizes a coaxially aligned drive train, the motor could be arranged in an offset or otherwise non-coaxial manner, relative to the longitudinal axis of the reservoir 205.

As best shown in FIG. 4, the drive screw 209 mates with threads 402 internal to the slide 206. When the motor assembly 207 is powered and operated, the drive screw 209 rotates, and the slide 206 is forced to translate in the axial direction 218. In an exemplary embodiment, the infusion pump 200 includes a sleeve 211 to prevent the slide 206 from rotating when the drive screw 209 of the drive system 208 rotates. Thus, rotation of the drive screw 209 causes the slide 206 to extend or retract relative to the drive motor assembly 207. When the fluid infusion device is assembled and operational, the slide 206 contacts the plunger 217 to engage the reservoir 205 and control delivery of fluid from the infusion pump 200. In an exemplary embodiment, the shoulder portion 215 of the slide 206 contacts or otherwise engages the plunger 217 to displace the plunger 217 in the axial direction 218. In alternative embodiments, the slide 206 may include a threaded tip 213 capable of being detachably engaged with internal threads 404 on the plunger 217 of the reservoir 205, as described in detail in U.S. Pat. Nos. 6,248,093 and 6,485,465, which are incorporated by reference herein.

As illustrated in FIG. 3, the electronics assembly 204 includes control electronics 224 coupled to the display element 226, with the housing 202 including a transparent window portion 228 that is aligned with the display element 226 to allow the display 226 to be viewed by the user when the electronics assembly 204 is disposed within the interior 214 of the housing 202. The control electronics 224 generally represent the hardware, firmware, processing logic and/or software (or combinations thereof) configured to control operation of the motor assembly 207 and/or drive system 208, as described in greater detail below in the context of FIG. 5. Whether such functionality is implemented as hardware, firmware, a state machine, or software depends upon the particular application and design constraints imposed on the embodiment. Those familiar with the concepts described here may implement such functionality in a suitable manner for each particular application, but such implementation decisions should not be interpreted as being restrictive or limiting. In an exemplary embodiment, the control electronics 224 includes one or more programmable controllers that may be programmed to control operation of the infusion pump 200.

The motor assembly 207 includes one or more electrical leads 236 adapted to be electrically coupled to the electronics assembly 204 to establish communication between the control electronics 224 and the motor assembly 207. In response to command signals from the control electronics 224 that operate a motor driver (e.g., a power converter) to regulate the amount of power supplied to the motor from a power supply, the motor actuates the drive train components of the drive system 208 to displace the slide 206 in the axial direction 218 to force fluid from the reservoir 205 along a fluid path (including tubing 221 and an infusion set), thereby administering doses of the fluid contained in the reservoir 205 into the user's body. Preferably, the power supply is realized one or more batteries contained within the housing 202. Alternatively, the power supply may be a solar panel, capacitor, AC or DC power supplied through a power cord, or the like. In some embodiments, the control electronics 224 may operate the motor of the motor assembly 207 and/or drive system 208 in a stepwise manner, typically on an intermittent basis; to administer discrete precise doses of the fluid to the user according to programmed delivery profiles.

Referring to FIGS. 2-4, as described above, the user interface 230 includes HMI elements, such as buttons 232 and a directional pad 234, that are formed on a graphic keypad overlay 231 that overlies a keypad assembly 233, which includes features corresponding to the buttons 232, directional pad 234 or other user interface items indicated by the graphic keypad overlay 231. When assembled, the keypad assembly 233 is coupled to the control electronics 224, thereby allowing the HMI elements 232, 234 to be manipulated by the user to interact with the control electronics 224 and control operation of the infusion pump 200, for example, to administer a bolus of insulin, to change therapy settings, to change user preferences, to select display features, to set or disable alarms and reminders, and the like. In this regard, the control electronics 224 maintains and/or provides information to the display 226 regarding program parameters, delivery profiles, pump operation, alarms, warnings, statuses, or the like, which may be adjusted using the HMI elements 232, 234. In various embodiments, the HMI elements 232, 234 may be realized as physical objects (e.g., buttons, knobs, joysticks, and the like) or virtual objects (e.g., using touch-sensing and/or proximity-sensing technologies). For example, in some embodiments, the display 226 may be realized as a touch screen or touch-sensitive display, and in such embodiments, the features and/or functionality of the HMI elements 232, 234 may be integrated into the display 226 and the HMI 230 may not be present. In some embodiments, the electronics assembly 204 may also include alert generating elements coupled to the control electronics 224 and suitably configured to generate one or more types of feedback, such as, without limitation: audible feedback; visual feedback; haptic (physical) feedback; or the like.

Referring to FIGS. 3-4, in accordance with one or more embodiments, the sensor assembly 210 includes a back plate structure 250 and a loading element 260. The loading element 260 is disposed between the capping member 212 and a beam structure 270 that includes one or more beams having sensing elements disposed thereon that are influenced by compressive force applied to the sensor assembly 210 that deflects the one or more beams, as described in greater detail in U.S. Pat. No. 8,474,332, which is incorporated by reference herein. In exemplary embodiments, the back plate structure 250 is affixed, adhered, mounted, or otherwise mechanically coupled to the bottom surface 238 of the drive system 208 such that the back plate structure 250 resides between the bottom surface 238 of the drive system 208 and the housing cap 216. The drive system capping member 212 is contoured to accommodate and conform to the bottom of the sensor assembly 210 and the drive system 208. The drive system capping member 212 may be affixed to the interior of the housing 202 to prevent displacement of the sensor assembly 210 in the direction opposite the direction of force provided by the drive system 208 (e.g., the direction opposite direction 218). Thus, the sensor assembly 210 is positioned between the motor assembly 207 and secured by the capping member 212, which prevents displacement of the sensor assembly 210 in a downward direction opposite the direction of arrow 218, such that the sensor assembly 210 is subjected to a reactionary compressive force when the drive system 208 and/or motor assembly 207 is operated to displace the slide 206 in the axial direction 218 in opposition to the fluid pressure in the reservoir 205. Under normal operating conditions, the compressive force applied to the sensor assembly 210 is correlated with the fluid pressure in the reservoir 205. As shown, electrical leads 240 are adapted to electrically couple the sensing elements of the sensor assembly 210 to the electronics assembly 204 to establish communication to the control electronics 224, wherein the control electronics 224 are configured to measure, receive, or otherwise obtain electrical signals from the sensing elements of the sensor assembly 210 that are indicative of the force applied by the drive system 208 in the axial direction 218.

Figure 5:
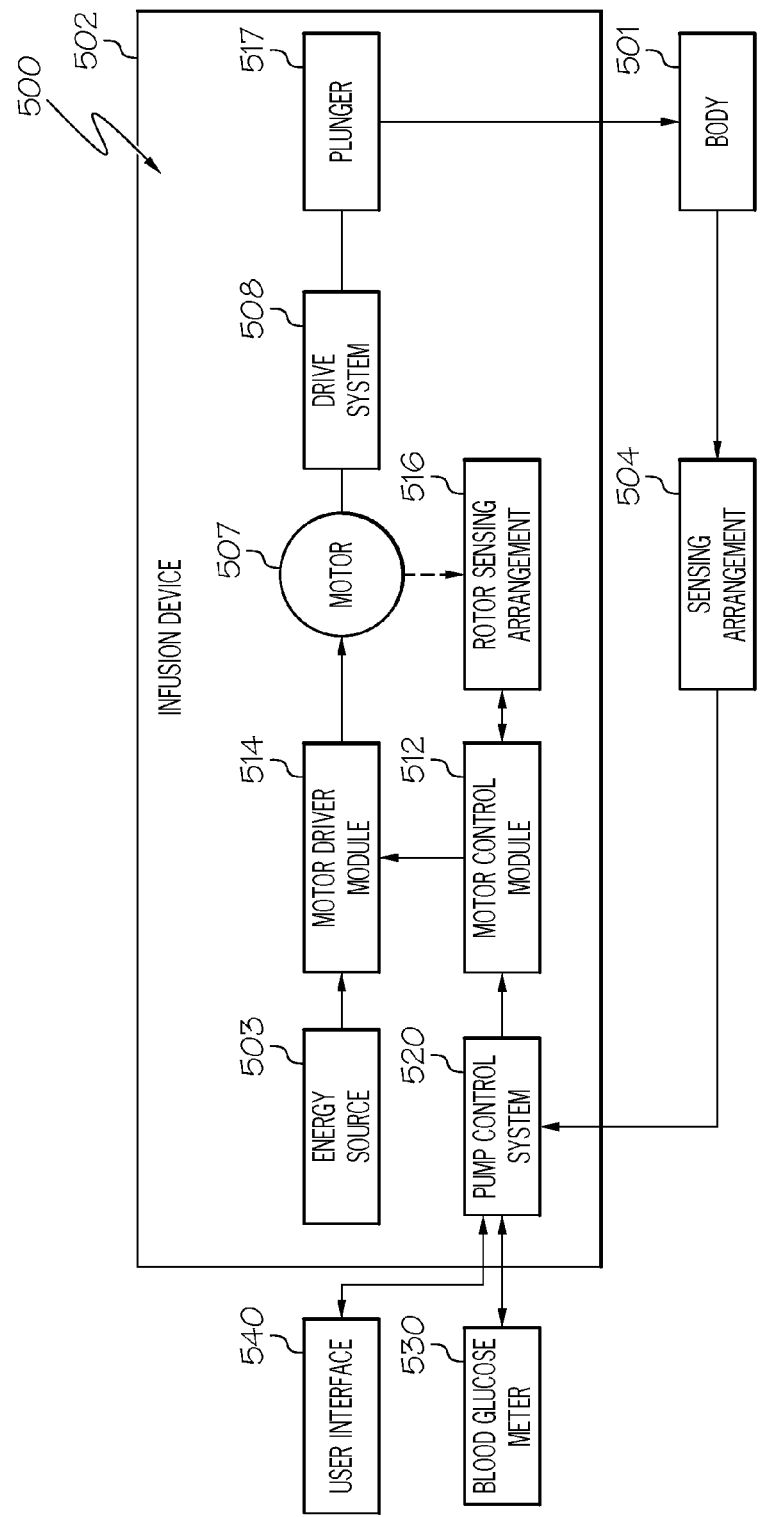
FIG. 5 is a block diagram of an exemplary control system suitable for use in a fluid infusion device, such as the fluid infusion device of FIG. 1 or FIG. 2.

FIG. 5 depicts an exemplary embodiment of a control system 500 suitable for use with an infusion device 502, such as the infusion device 102 in FIG. 1 or the infusion device 200 of FIG. 2. The control system 500 is capable of controlling or otherwise regulating a physiological condition in the body 501 of a user to a desired (or target) value or otherwise maintain the condition within a range of acceptable values in an automated or autonomous manner. In one or more exemplary embodiments, the condition being regulated is sensed, detected, measured or otherwise quantified by a sensing arrangement 504 (e.g., sensing arrangement 104) communicatively coupled to the infusion device 502. However, it should be noted that in alternative embodiments, the condition being regulated by the control system 500 may be correlative to the measured values obtained by the sensing arrangement 504. That said, for clarity and purposes of explanation, the subject matter may be described herein in the context of the sensing arrangement 504 being realized as a glucose sensing arrangement that senses, detects, measures or otherwise quantifies the user's glucose level, which is being regulated in the body 501 of the user by the control system 500.

In exemplary embodiments, the sensing arrangement 504 includes one or more interstitial glucose sensing elements that generate or otherwise output electrical signals having a signal characteristic that is correlative to, influenced by, or otherwise indicative of the relative interstitial fluid glucose level in the body 501 of the user. The output electrical signals are filtered or otherwise processed to obtain a measurement value indicative of the user's interstitial fluid glucose level. In exemplary embodiments, a blood glucose meter 530, such as a finger stick device, is utilized to directly sense, detect, measure or otherwise quantify the blood glucose in the body 501 of the user. In this regard, the blood glucose meter 530 outputs or otherwise provides a measured blood glucose value that may be utilized as a reference measurement for calibrating the sensing arrangement 504 and converting a measurement value indicative of the user's interstitial fluid glucose level into a corresponding calibrated blood glucose value. For purposes of explanation, the calibrated blood glucose value calculated based on the electrical signals output by the sensing element(s) of the sensing arrangement 504 may alternatively be referred to herein as the sensor glucose value, the sensed glucose value, or variants thereof.

In the illustrated embodiment, the pump control system 520 generally represents the electronics and other components of the infusion device 502 that control operation of the fluid infusion device 502 according to a desired infusion delivery program in a manner that is influenced by the sensed glucose value indicative of a current glucose level in the body 501 of the user. For example, to support a closed-loop operating mode, the pump control system 520 maintains, receives, or otherwise obtains a target or commanded glucose value, and automatically generates or otherwise determines dosage commands for operating an actuation arrangement, such as a motor 507, to displace the plunger 517 and deliver insulin to the body 501 of the user based on the difference between a sensed glucose value and the target glucose value. In other operating modes, the pump control system 520 may generate or otherwise determine dosage commands configured to maintain the sensed glucose value below an upper glucose limit, above a lower glucose limit, or otherwise within a desired range of glucose values. In practice, the infusion device 502 may store or otherwise maintain the target value, upper and/or lower glucose limit (s), and/or other glucose threshold value(s) in a data storage element accessible to the pump control system 520.

The target glucose value and other threshold glucose values may be received from an external component (e.g., CCD 106 and/or computing device 108) or be input by a user via a user interface element 540 associated with the infusion device 502. In practice, the one or more user interface element(s) 540 associated with the infusion device 502 typically include at least one input user interface element, such as, for example, a button, a keypad, a keyboard, a knob, a joystick, a mouse, a touch panel, a touchscreen, a microphone or another audio input device, and/or the like. Additionally, the one or more user interface element(s) 540 include at least one output user interface element, such as, for example, a display element (e.g., a light-emitting diode or the like), a display device (e.g., a liquid crystal display or the like), a speaker or another audio output device, a haptic feedback device, or the like, for providing notifications or other information to the user. It should be noted that although FIG. 5 depicts the user interface element(s) 540 as being separate from the infusion device 502, in practice, one or more of the user interface element(s) 540 may be integrated with the infusion device 502. Furthermore, in some embodiments, one or more user interface element(s) 540 are integrated with the sensing arrangement 504 in addition to and/or in alternative to the user interface element(s) 540 integrated with the infusion device 502. The user interface element(s) 540 may be manipulated by the user to operate the infusion device 502 to deliver correction boluses, adjust target and/or threshold values, modify the delivery control scheme or operating mode, and the like, as desired.

Still referring to FIG. 5, in the illustrated embodiment, the infusion device 502 includes a motor control module 512 coupled to a motor 507 (e.g., motor assembly 207) that is operable to displace a plunger 517 (e.g., plunger 217) in a reservoir (e.g., reservoir 205) and provide a desired amount of fluid to the body 501 of a user. In this regard, displacement of the plunger 517 results in the delivery of a fluid that is capable of influencing the condition in the body 501 of the user to the body 501 of the user via a fluid delivery path (e.g., via tubing 221 of an infusion set 225). A motor driver module 514 is coupled between an energy source 503 and the motor 507. The motor control module 512 is coupled to the motor driver module 514, and the motor control module 512 generates or otherwise provides command signals that operate the motor driver module 514 to provide current (or power) from the energy source 503 to the motor 507 to displace the plunger 517 in response to receiving, from a pump control system 520, a dosage command indicative of the desired amount of fluid to be delivered.

In exemplary embodiments, the energy source 503 is realized as a battery housed within the infusion device 502 (e.g., within housing 202) that provides direct current (DC) power. In this regard, the motor driver module 514 generally represents the combination of circuitry, hardware and/or other electrical components configured to convert or otherwise transfer DC power provided by the energy source 503 into alternating electrical signals applied to respective phases of the stator windings of the motor 507 that result in current flowing through the stator windings that generates a stator magnetic field and causes the rotor of the motor 507 to rotate. The motor control module 512 is configured to receive or otherwise obtain a commanded dosage from the pump control system 520, convert the commanded dosage to a commanded translational displacement of the plunger 517, and command, signal, or otherwise operate the motor driver module 514 to cause the rotor of the motor 507 to rotate by an amount that produces the commanded translational displacement of the plunger 517. For example, the motor control module 512 may determine an amount of rotation of the rotor required to produce translational displacement of the plunger 517 that achieves the commanded dosage received from the pump control system 520. Based on the current rotational position (or orientation) of the rotor with respect to the stator that is indicated by the output of the rotor sensing arrangement 516, the motor control module 512 determines the appropriate sequence of alternating electrical signals to be applied to the respective phases of the stator windings that should rotate the rotor by the determined amount of rotation from its current position (or orientation). In embodiments where the motor 507 is realized as a BLDC motor, the alternating electrical signals commutate the respective phases of the stator windings at the appropriate orientation of the rotor magnetic poles with respect to the stator and in the appropriate order to provide a rotating stator magnetic field that rotates the rotor in the desired direction. Thereafter, the motor control module 512 operates the motor driver module 514 to apply the determined alternating electrical signals (e.g., the command signals) to the stator windings of the motor 507 to achieve the desired delivery of fluid to the user.

When the motor control module 512 is operating the motor driver module 514, current flows from the energy source 503 through the stator windings of the motor 507 to produce a stator magnetic field that interacts with the rotor magnetic field. In some embodiments, after the motor control module 512 operates the motor driver module 514 and/or motor 507 to achieve the commanded dosage, the motor control module 512 ceases operating the motor driver module 514 and/or motor 507 until a subsequent dosage command is received. In this regard, the motor driver module 514 and the motor 507 enter an idle state during which the motor driver module 514 effectively disconnects or isolates the stator windings of the motor 507 from the energy source 503. In other words, current does not flow from the energy source 503 through the stator windings of the motor 507 when the motor 507 is idle, and thus, the motor 507 does not consume power from the energy source 503 in the idle state, thereby improving efficiency.

Depending on the embodiment, the motor control module 512 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In exemplary embodiments, the motor control module 512 includes or otherwise accesses a data storage element or memory, including any sort of random access memory (RAM), read only memory (ROM), flash memory, registers, hard disks, removable disks, magnetic or optical mass storage, or any other short or long term storage media or other non-transitory computer-readable medium, which is capable of storing programming instructions for execution by the motor control module 512. The computer-executable programming instructions, when read and executed by the motor control module 512, cause the motor control module 512 to perform or otherwise support the tasks, operations, functions, and processes described herein.

It should be appreciated that FIG. 5 is a simplified representation of the infusion device 502 for purposes of explanation and is not intended to limit the subject matter described herein in any way. In this regard, depending on the embodiment, some features and/or functionality of the sensing arrangement 504 may implemented by or otherwise integrated into the pump control system 520, or vice versa. Similarly, in practice, the features and/or functionality of the motor control module 512 may implemented by or otherwise integrated into the pump control system 520, or vice versa. Furthermore, the features and/or functionality of the pump control system 520 may be implemented by control electronics 224 located in the fluid infusion device 200, 400, while in alternative embodiments, the pump control system 520 may be implemented by a remote computing device that is physically distinct and/or separate from the infusion device 502, such as, for example, the CCD 106 or the computing device 108.

Figure 6:
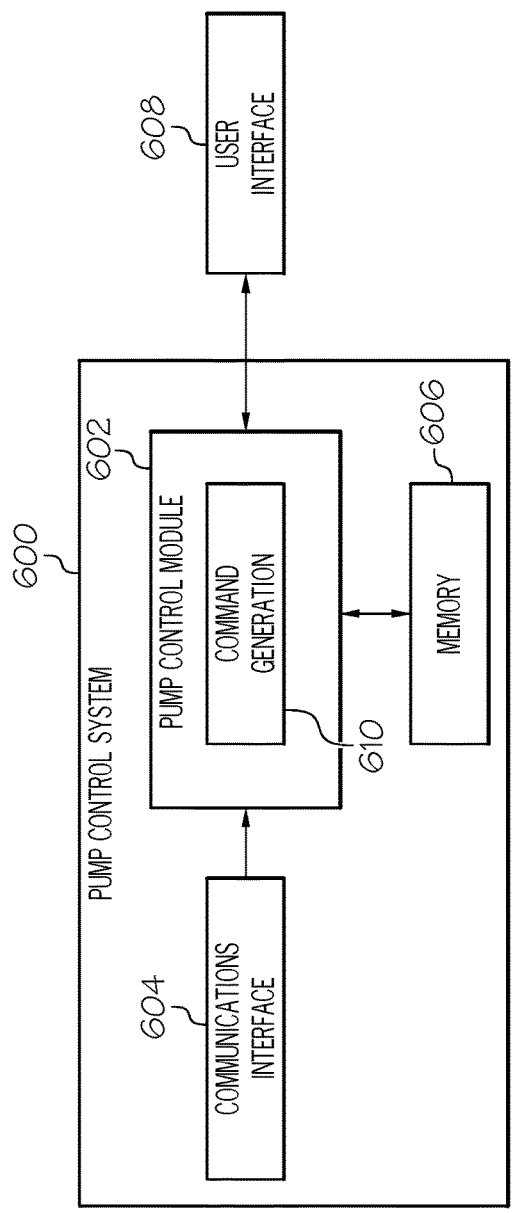
FIG. 6 is a block diagram of an exemplary pump control system suitable for use in the control system of FIG. 5.

FIG. 6 depicts an exemplary embodiment of a pump control system 600 suitable for use as the pump control system 520 in FIG. 5 in accordance with one or more embodiments. The illustrated pump control system 600 includes, without limitation, a pump control module 602, a communications interface 604, and a data storage element (or memory) 606. The pump control module 602 is coupled to the communications interface 604 and the memory 606, and the pump control module 602 is suitably configured to support the operations, tasks, and/or processes described herein. In exemplary embodiments, the pump control module 602 is also coupled to one or more user interface elements 608 (e.g., user interface 230, 540) for receiving user input and providing notifications, alerts, or other therapy information to the user. Although FIG. 6 depicts the user interface element 608 as being separate from the pump control system 600, in various alternative embodiments, the user interface element 608 may be integrated with the pump control system 600 (e.g., as part of the infusion device 200, 502), the sensing arrangement 504 or another element of an infusion system 100 (e.g., the computer 108 or CCD 106).

Referring to FIG. 6 and with reference to FIG. 5, the communications interface 604 generally represents the hardware, circuitry, logic, firmware and/or other components of the pump control system 600 that are coupled to the pump control module 602 and configured to support communications between the pump control system 600 and the sensing arrangement 504. In this regard, the communications interface 604 may include or otherwise be coupled to one or more transceiver modules capable of supporting wireless communications between the pump control system 520, 600 and the sensing arrangement 504 or another electronic device 106, 108 in an infusion system 100. In other embodiments, the communications interface 604 may be configured to support wired communications to/from the sensing arrangement 504.

The pump control module 602 generally represents the hardware, circuitry, logic, firmware and/or other component of the pump control system 600 that is coupled to the communications interface 604 and configured to determine dosage commands for operating the motor 506 to deliver fluid to the body 501 based on data received from the sensing arrangement 504 and perform various additional tasks, operations, functions and/or operations described herein. For example, in exemplary embodiments, pump control module 602 implements or otherwise executes a command generation application 610 that supports one or more autonomous operating modes and calculates or otherwise determines dosage commands for operating the motor 506 of the infusion device 502 in an autonomous operating mode based at least in part on a current measurement value for a condition in the body 501 of the user. For example, in a closed-loop operating mode, the command generation application 610 may determine a dosage command for operating the motor 506 to deliver insulin to the body 501 of the user based at least in part on the current glucose measurement value most recently received from the sensing arrangement 504 to regulate the user's blood glucose level to a target reference glucose value.

Additionally, the command generation application 610 may generate dosage commands for boluses that are manually-initiated or otherwise instructed by a user via a user interface element 608. For example, independent of the operating mode being implemented, the command generation application 610 may determine a dosage command for operating the motor 506 to deliver a bolus of insulin to the body 501 of the user that corresponds to a correction bolus or meal bolus amount selected or otherwise indicated by the user via the user interface element 230, 540, 608. In one or more exemplary embodiments described herein, to initiate a meal bolus, the user manipulates the user interface element 230, 540, 608 to input or otherwise provide an indication of an amount of grams of carbohydrates which are expected to be consumed in connection with an impending meal. The command generation application 610 receives the input carbohydrate amount (CHO) and retrieves or otherwise obtains a carbohydrate conversion ratio associated with the user from a data storage element 606 (or memory), which, in turn, is utilized to convert the input carbohydrate amount into a corresponding bolus amount of insulin units using the equation $$U_{meal} = \frac{CHO}{CR},$$

where CR is the patient-specific carbohydrate ratio in terms of grams of carbohydrates per insulin unit. In one or more embodiments, the memory 606 stores a plurality of different patient-specific carbohydrate ratios, with each carbohydrate ratio being associated with a particular bolus context, such as, for example, a particular time of day (e.g., a 6 AM-10 AM time window, a 10 AM-2 PM time window, and the like). Additionally, the carbohydrate ratios may be associated with particular days of the week, or other variables or parameters that may be input by the user or otherwise detected automatically, such as, for example, whether or not the user has engaged in a particular type or duration of activity within a preceding time period. After determining the bolus dosage amount for the input carbohydrate amount using the appropriate carbohydrate ratio, the command generation application 610 may provide the commanded bolus dosage to the motor control module 512, which, in turn, converts the commanded dosage into a corresponding displacement of the plunger 517 and operates the motor 507 accordingly to deliver the meal bolus with the commanded dosage amount.

As described in greater detail below in the context of FIGS. 7-10, in one or more embodiments, the command generation application 610 stores or otherwise maintains the most recently received sensor glucose measurement at the time of delivery of the meal bolus (e.g., the current pre-prandial glucose measurement value at the time of the bolus) and then monitors or otherwise analyzes subsequently received sensor glucose measurement values to detect or otherwise identify a post-prandial settling value after the user's glucose level recovers from a post-prandial peak value. In this regard, the command generation application 610 may identify a nadir or inflection point in the sensor glucose measurement values occurring after a peak value following the meal bolus delivery. Based on the difference between the post-prandial settling value and the stored pre-prandial value, the command generation application 610 determines a residual sensor glucose value ($\Delta SG_R$) and updates the identified carbohydrate ratio used for the delivered meal bolus by adjusting the ratio in a manner that compensates for the residual sensor glucose value. In this regard, the command generation application 610 determines an adjustment scaling factor based on the residual sensor glucose value, which is then utilize to scale the carbohydrate ratio up or down as appropriate to compensate for the residual glucose value. The updated carbohydrate ratio value is then stored in the memory 606 in lieu of the previous value for the identified carbohydrate ratio associated with the current bolus context. Thus, for a subsequent meal bolus having the same bolus context, the updated carbohydrate ratio is utilized to determine that subsequent meal bolus, and the carbohydrate ratio may be further updated or adjusted based on the residual glucose value attributable to that subsequent meal bolus, and so on. In this manner, carbohydrate ratios are adaptively and dynamically adjusted towards a value that minimizes the post-prandial residual glucose value.

Still referring to FIG. 6, depending on the embodiment, the pump control module 602 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In this regard, the steps of a method or algorithm described in connection with the embodiments disclosed herein may be embodied directly in hardware, in firmware, in a software module executed by the pump control module 602, or in any practical combination thereof. In exemplary embodiments, the pump control module 602 includes or otherwise accesses the data storage element or memory 606, which may be realized using any sort of non-transitory computer-readable medium capable of storing programming instructions for execution by the pump control module 602. The computer-executable programming instructions, when read and executed by the pump control module 602, cause the pump control module 602 to implement or otherwise generate the command generation application 610 and perform the tasks, operations, functions, and processes described in greater detail below.

It should be understood that FIG. 6 is a simplified representation of a pump control system 600 for purposes of explanation and is not intended to limit the subject matter described herein in any way. For example, in some embodiments, the features and/or functionality of the motor control module 512 may be implemented by or otherwise integrated into the pump control system 600 and/or the pump control module 602, for example, by the command generation application 610 converting the dosage command into a corresponding motor command, in which case, the separate motor control module 512 may be absent from an embodiment of the infusion device 502.

Figure 7:
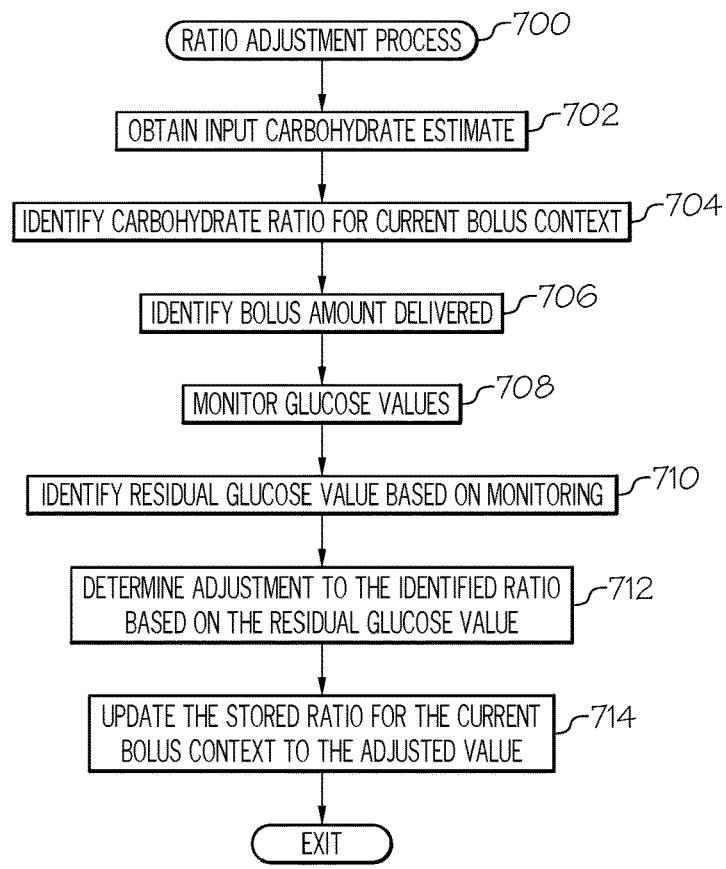
FIG. 7 is a flow diagram of an exemplary adaptive ratio adjustment process suitable for use with the control system of FIG. 5 in one or more exemplary embodiments.

FIG. 7 depicts an exemplary ratio adjustment process 700 suitable for implementation by a control system associated with a fluid infusion device, such as a control system 500, 520, 600 in the infusion device 502, to automatically adjust the conversion ratio(s) used for determining bolus amounts in a manner that accounts for the effect of a preceding bolus when determining a subsequent bolus amount. The various tasks performed in connection with the ratio adjustment process 700 may be performed by hardware, firmware, software executed by processing circuitry, or any combination thereof. For illustrative purposes, the following description refers to elements mentioned above in connection with FIGS. 1-6. In practice, portions of the ratio adjustment process 700 may be performed by different elements of the control system 500, such as, for example, the infusion device 502, the sensing arrangement 504, the pump control system 520, 600, the pump control module 602, and/or the command generation application 610. It should be appreciated that the ratio adjustment process 700 may include any number of additional or alternative tasks, the tasks need not be performed in the illustrated order and/or the tasks may be performed concurrently, and/or the ratio adjustment process 700 may be incorporated into a more comprehensive procedure or process having additional functionality not described in detail herein. Moreover, one or more of the tasks shown and described in the context of FIG. 7 could be omitted from a practical embodiment of the ratio adjustment process 700 as long as the intended overall functionality remains intact.

Referring to FIG. 7 with continued reference to FIGS. 1-6, in exemplary embodiments, the ratio adjustment process 700 is performed each time an infusion device is operated to deliver a manually-initiated bolus, such as a meal or correction bolus. The ratio adjustment process 700 begins by receiving, identifying, or otherwise obtaining the input carbohydrate estimate for a bolus to be delivered (task 702). In this regard, the pump control system 520, 600 receives or otherwise obtains, via the user interface 540, 608, an estimate of the amount of grams of carbohydrates that the user anticipates he or she will be consuming. The ratio adjustment process 700 also identifies or otherwise obtains the appropriate carbohydrate ratio utilized to convert the input carbohydrate amount to an amount of insulin units for the bolus (task 704). In this regard, the ratio adjustment process 700 may identify or otherwise determine the current bolus context (e.g., the current time of day, the current day of the week, and the like), and then select or otherwise identify the carbohydrate ratio associated with the current bolus context. For example, a number of different carbohydrate ratios associated with the user may be stored in association with different time periods or windows during the day, with the pump control module 602 identifying or otherwise determining which time period encompasses the current infusion time and retrieving the corresponding carbohydrate ratio from the memory 606.

The ratio adjustment process 700 also identifies or determines the amount of the bolus being delivered for the current infusion (task 706). For example, the pump control system 520, 600 may determine the bolus amount using the equation $$U_{meal} = \frac{CHO}{CR},$$

where CR is the patient-specific carbohydrate ratio in terms of grams of carbohydrates per insulin unit for the current time of day (or other criteria or parameters associated with the current bolus context) and CHO is the input grams of carbohydrate amount to be corrected by the bolus.

The ratio adjustment process 700 monitors or otherwise analyzes the user's sensor glucose measurement values, and based thereon, identifies or otherwise determines a residual glucose value attributable to the delivered bolus (tasks 708, 710). In this regard, upon delivery of the bolus, the pump control system 520, 600 may store or otherwise maintain the current glucose measurement value most recently received from the sensing arrangement 504 prior to delivery of the bolus as a pre-prandial reference glucose value ($SG_0$). Thereafter, the pump control system 520, 600 monitors or otherwise analyzes the glucose measurement values received from the sensing arrangement 504 after to delivery of the bolus to identify a peak post-prandial glucose value. After the peak post-prandial glucose value is identified, the pump control system 520, 600 monitors or otherwise analyzes the glucose measurement values received from the sensing arrangement 504 to identify a settling value or nadir in the glucose measurement values that represents the user's glucose level after metabolizing the consumed meal, the meal bolus, and any other insulin infused by any other autonomous control modes currently being implemented by the pump control system 520, 600. The identified value functions as a post-prandial reference glucose value ($SG_{pp}$) used for determining the residual glucose value ($MG_R$) as the difference between the post-prandial reference glucose value and the pre-prandial reference glucose value (e.g., $\Delta SG_R = SG_{pp} - SG_0$).

In one or more embodiments, the pump control system 520, 600 monitors or otherwise analyzes the rate of change between successive glucose measurement values to identify the post-prandial reference glucose value based on an inflection point after the post-prandial peak where the rate of change transitions from a negative rate of change after the post-prandial peak to a rate of change greater than or equal to 0, thereby indicating a nadir or settling of the user's glucose level. In this regard, the identified sensor glucose value where the user's glucose level initially stops falling after the post-prandial peak functions as the post-prandial reference glucose value. In other embodiments, the pump control system 520, 600 monitors the glucose measurement values over a fixed duration of time after the delivery of the bolus and identifies the minimum sensor glucose value occurring after the post-prandial peak value within that fixed duration of time as the post-prandial reference glucose value.

Figure 8:
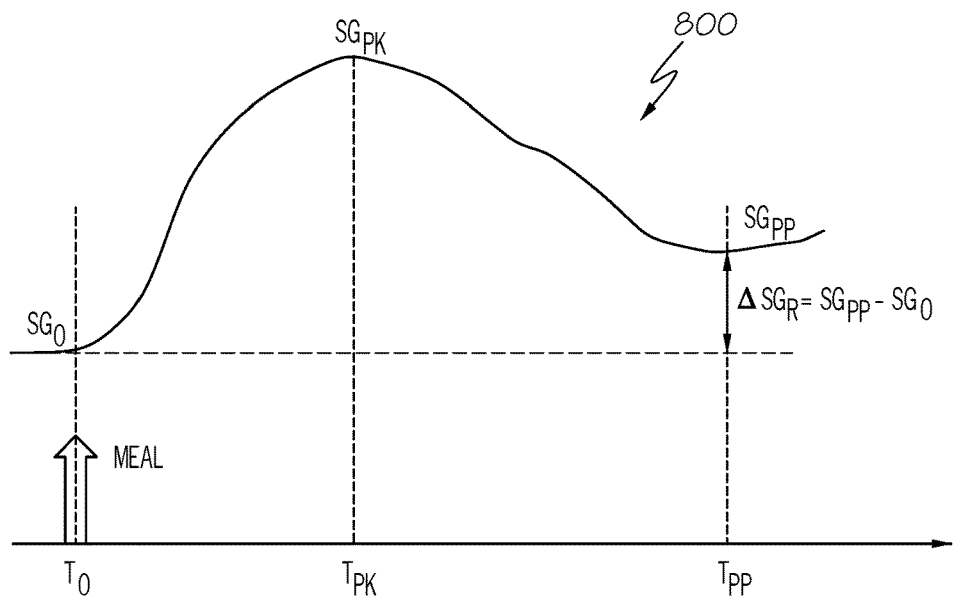
FIG. 8 is a graph depicting an exemplary relationship between an individual's post-prandial glucose level and time.

FIG. 8 is a graph 800 depicting an exemplary relationship of a user's sensor glucose values with respect to time after administering a bolus at or around the time of a meal. At an initial time ($T_0$), the infusion device 502 delivers a meal bolus amount of insulin determined based on the input carbohydrate amount and the identified carbohydrate ratio for the current bolus context (e.g., a carbohydrate ratio associated with a time window encompassing $T_0$). The pump control system 520, 600 stores or otherwise maintains the current sensor glucose value most recently received from the sensing arrangement 504 at the bolus time ($SG_0$) as the pre-prandial sensor glucose reference value and monitors or otherwise analyzes subsequent sensor glucose values from the sensing arrangement 504 to detect or otherwise identify a peak sensor glucose value ($SG_{PK}$) at time $T_{PK}$. Thereafter, in one or more embodiments, the pump control system 520, 600 monitors or otherwise analyzes the rate of change between successive sensor glucose values until identifying an inflection point at time $T_{PK}$. The pump control system 520, 600 identifies the current sensor glucose value at time $T_{PK}$ as the post-prandial sensor glucose reference value ($SG_{pp}$) and determines the residual sensor glucose value as the difference between the post-prandial and pre-prandial sensor glucose reference values, as described above. In other embodiments, the pump control system 520, 600 monitors or otherwise analyzes the sensor glucose measurement values for a fixed period of time after bolus time $T_0$, and identifies the post-prandial sensor glucose reference value as the minimum sensor glucose value within that fixed period of time that occurs after the peak sensor glucose value ($SG_{PK}$) at time $T_{PK}$.

Referring again to FIG. 7, after identifying a residual glucose value, the ratio adjustment process 700 calculates or otherwise determines an adjustment for the previously identified carbohydrate ratio used for the bolus that was delivered based on the residual glucose value and then updates the carbohydrate ratio stored or otherwise maintained onboard the infusion device to reflect the adjustment (tasks 712, 714). In exemplary embodiments, the pump control system 520, 600 uses the residual glucose value to calculate an adjustment factor configured to compensate for the residual glucose value and then scales previously identified carbohydrate ratio by the adjustment factor to obtain an updated value for the identified carbohydrate ratio, which, in turn is stored in the memory 606 in lieu of the previous value for the identified carbohydrate ratio.

Thereafter, in response to receiving, via the user interface 540, 608, an estimate of an amount of grams of carbohydrates associated with a subsequent meal having the same bolus context, the pump control system 520, 600 uses the updated value for that carbohydrate ratio to convert the input carbohydrate amount for that subsequent meal to a corresponding bolus amount using the equation $$U_{meal} = \frac{CHO}{CR},$$

where CR is the updated value for the identified carbohydrate ratio and CHO is the input carbohydrate amount. In this regard, when the input carbohydrate amount for the subsequent meal is the same as the preceding meal having the same bolus context, the resulting meal bolus amount will be different than the preceding bolus amount to account for the change in the carbohydrate ratio value intended to compensate for the residual glucose after the preceding bolus. Additionally, the ratio adjustment process 700 may be repeated in conjunction with the subsequent bolus to further update or adjust the carbohydrate ratio value in a manner that accounts for the residual glucose resulting from the subsequent bolus. In this manner, the carbohydrate ratio is adaptively and dynamically adjusted to account for the effectiveness of the preceding boluses, which, in turn, may reduce the residual glucose associated with subsequent boluses, thereby minimizing post-prandial glucose excursions and improving glucose regulation.

FIG. 9 depicts an exemplary sensitivity factor adjustment process 900 suitable for use in conjunction with the ratio adjustment process 700 of FIG. 7 (e.g., task 712) to update a carbohydrate ratio value based on a residual glucose value. The various tasks performed in connection with the sensitivity factor adjustment process 900 may be performed by hardware, firmware, software executed by processing circuitry, or any combination thereof. For illustrative purposes, the following description refers to elements mentioned above in connection with FIGS. 1-6. In practice, portions of the sensitivity factor adjustment process 900 may be performed by different elements of the control system 500, such as, for example, the infusion device 502, the sensing arrangement 504, the pump control system 520, 600, the pump control module 602, and/or the command generation application 610. It should be appreciated that the sensitivity factor adjustment process 900 may include any number of additional or alternative tasks, the tasks need not be performed in the illustrated order and/or the tasks may be performed concurrently, and/or the sensitivity factor adjustment process 900 may be incorporated into a more comprehensive procedure or process having additional functionality not described in detail herein. Moreover, one or more of the tasks shown and described in the context of FIG. 9 could be omitted from a practical embodiment of the sensitivity factor adjustment process 900 as long as the intended overall functionality remains intact.

The sensitivity factor adjustment process 900 identifies or otherwise obtains a patient-specific insulin sensitivity factor and converts the residual sensor glucose value to a corresponding amount of units of insulin based on the insulin sensitivity factor (tasks 902, 904). In this regard, the pump control system 520, 600 determines a residual insulin amount corresponding to the residual sensor glucose value using the equation $$U_R = \frac{\Delta SG_R}{ISF},$$

where ISF represents the user's insulin sensitivity factor value (in milligrams per deciliter per units when the residual sensor glucose value is in milligrams per deciliter) that is stored or otherwise maintained onboard the infusion device 502 (e.g., in memory 606). In a similar manner as described above, in some embodiments, the infusion device 502 may maintain a plurality of different insulin sensitivity factors associated with different delivery contexts, where the pump control system 520, 600 identifies the insulin sensitivity factor that corresponds to the current bolus context from among the plurality of different insulin sensitivity factors. Thus, depending on the time of day, day of the week, and the like, the relationship between the residual insulin amount and the residual sensor glucose value may vary in a manner that reflects the user's insulin sensitivity contemporaneous to the bolus being delivered.

Thereafter, the sensitivity factor adjustment process 900 adjusts, modifies, or otherwise updates the carbohydrate ratio used to determine the preceding bolus amount based on the residual insulin amount (task 906). In exemplary embodiments, the pump control system 520, 600 calculates an adjustment factor based on the relationship (or ratio) of the preceding meal bolus amount to the sum of the preceding meal bolus amount and the residual insulin amount. The adjustment factor may be determined using the equation $$\frac{U_{meal}}{U_{meal} + U_R},$$

where $U_{meal}$ represents the delivered meal bolus amount and $U_R$ represents the residual insulin amount. The updated carbohydrate ratio value is calculated by scaling the current carbohydrate value by the adjustment factor using the equation $$CR_{New} = CR_{Old}\left(\frac{U_{meal}}{U_{meal} + U_R}\right),$$

where $CR_{New}$ represents the updated carbohydrate ratio value and $CR_{Old}$ represents the carbohydrate ratio value used to determine the delivered meal bolus amount. In this regard, a positive residual insulin amount decreases the carbohydrate ratio value, which, in turn, will increase a subsequently determined meal bolus amount for the same input amount of carbohydrates to thereby reduce the subsequent residual glucose value. Conversely, a negative residual insulin amount increases the carbohydrate ratio value, which, in turn, will decrease a subsequently determined meal bolus amount for the same input amount of carbohydrates to thereby reduce the magnitude of the subsequent residual glucose value.

FIG. 10 depicts an exemplary conversion factor adjustment process 1000 suitable for use in conjunction with the ratio adjustment process 700 of FIG. 7 (e.g., task 712) to update a carbohydrate ratio value based on a residual glucose value. The various tasks performed in connection with the conversion factor adjustment process 1000 may be performed by hardware, firmware, software executed by processing circuitry, or any combination thereof. For illustrative purposes, the following description refers to elements mentioned above in connection with FIGS. 1-6. In practice, portions of the conversion factor adjustment process 1000 may be performed by different elements of the control system 500, such as, for example, the infusion device 502, the sensing arrangement 504, the pump control system 520, 600, the pump control module 602, and/or the command generation application 610. It should be appreciated that the conversion factor adjustment process 1000 may include any number of additional or alternative tasks, the tasks need not be performed in the illustrated order and/or the tasks may be performed concurrently, and/or the conversion factor adjustment process 1000 may be incorporated into a more comprehensive procedure or process having additional functionality not described in detail herein. Moreover, one or more of the tasks shown and described in the context of FIG. 10 could be omitted from a practical embodiment of the conversion factor adjustment process 1000 as long as the intended overall functionality remains intact.

The conversion factor adjustment process 1000 identifies or otherwise obtains a carbohydrate conversion factor for the user and converts the residual sensor glucose value to a corresponding amount of carbohydrates based on the carbohydrate conversion factor (tasks 1002, 1004). In this regard, the carbohydrate conversion factor represents the relationship between an increase in the user's glucose level per gram of carbohydrate consumed. After identifying the carbohydrate conversion factor, the pump control system 520, 600 determines a residual amount of grams of carbohydrates corresponding to the residual sensor glucose value using the equation $$CHO_R = \frac{\Delta SG_R}{CF},$$

where CF represents the carbohydrate conversion factor value (in milligrams per deciliter per gram when the residual glucose value is in milligrams per deciliter).

In one embodiment, a lookup table is stored or otherwise maintained onboard the infusion device 502 (e.g., in memory 606) that is utilized by the pump control system 520, 600 to identify the carbohydrate conversion factor corresponding to the user. For example, the lookup table may include a plurality of different carbohydrate conversion factor values associated with a plurality of different body weights (or ranges thereof), with the pump control system 520, 600 identifying the carbohydrate conversion factor corresponding to the user's current weight, which may be input by the user and/or stored onboard the infusion device 502 as part of the user's individual profile or settings. In a similar manner as described above in the context of the carbohydrate ratio and the insulin sensitivity factor, the carbohydrate conversion factor values in the lookup table may be further associated with different delivery contexts, where the pump control system 520, 600 identifies the carbohydrate conversion factor value that corresponds to the current bolus context and the user's current weight (or other physiological condition) from among the plurality of different carbohydrate conversion factors. In other embodiments, in lieu of a lookup table, fixed carbohydrate conversion factor(s) may be manually configured by a user or care provider via the user interface 540, 608 and stored onboard the infusion device 502. In yet other embodiments, the pump control system 520, 600 may dynamically calculate or otherwise determine carbohydrate conversion factor values for the user based on the relationship between the user's sensor glucose values associated with meal consumption and the estimated carbohydrate amounts for those meals in a manner that accounts for the amount of meal boluses delivered.

Still referring to FIG. 10, after determining the residual carbohydrate amount, the conversion factor adjustment process 1000 adjusts, modifies, or otherwise updates the carbohydrate ratio used to determine the preceding bolus amount based on the residual carbohydrate amount (task 1006). In exemplary embodiments, the pump control system 520, 600 calculates an adjustment factor based on the relationship (or ratio) of the difference between the input carbohydrate amount corresponding to the preceding meal bolus amount and the residual carbohydrate amount with respect to the input carbohydrate amount. For example, the adjustment factor may be determined using the equation $$\frac{CHO_{Ann} - CHO_R}{CHO_{Ann}},$$

where $CHO_{Ann}$ represents the input carbohydrate estimate used to determine the delivered meal bolus amount and $CHO_R$ represents the residual carbohydrate amount. The updated carbohydrate ratio value is then calculated by scaling the current carbohydrate value by the adjustment factor using the equation $$CR_{New} = CR_{Old}\left(\frac{CHO_{Ann} - CHO_R}{CHO_{Ann}}\right),$$

where $CR_{New}$ represents the updated carbohydrate ratio value and $CR_{Old}$ represents the carbohydrate ratio value used to determine the delivered meal bolus amount. In this regard, a positive residual carbohydrate amount decreases the carbohydrate ratio value, which, in turn, will increase a subsequently determined meal bolus amount for the same input amount of carbohydrates to thereby reduce the subsequent residual glucose value. Conversely, a negative residual carbohydrate amount increases the carbohydrate ratio value, which, in turn, will decrease a subsequently determined meal bolus amount for the same input amount of carbohydrates to thereby reduce the magnitude of the subsequent residual glucose value.

To briefly summarize, the subject matter described above allows for a patient-specific carbohydrate ratio to be dynamically adjusted to account for the patient's observed response to a preceding bolus and reduce the post-prandial glucose excursions exhibited after subsequent meals and boluses. In this regard, not only does the carbohydrate ratio adapt to reflect the individual's physiological response to a bolus and accompanying meal, but also can account for the individual habitually overestimating or underestimating the amount of carbohydrates associated with meals. Additionally, carbohydrate ratios may be associated with different delivery contexts, with adjustments being specific to a particular delivery context, thereby facilitating bolus amounts that reflect the individual's likely physiological response for the current circumstances (e.g., time of day, day of week, etc.).

In some embodiments, the carbohydrate ratio may be preemptively adjusted before administration of a bolus based on historical trends in the adjustment factor with respect to the delivery context or other available information. For example, when boluses delivered at a particular time of day on a particular day of the week (e.g., evening meals on the weekend) exhibit an anomalous adjustment factor after the adjustment factor for other days of the week have converged towards a stable value (e.g., an adjustment factor value of approximately one), the carbohydrate ratio may be pre-adjusted to avoid a post-prandial glucose excursion. In this regard, the infusion device may store or otherwise maintain a set of the most recent adjustment factors and their associated context information which can be analyzed to detect or otherwise identify a bolus context for which pre-adjustment may be appropriate based on a difference in the adjustment factors for that bolus context deviating from other adjustment factors for a same or similar bolus context (e.g., the same time of day but different days of the week) by more than a threshold amount (e.g., a threshold percentage of the average adjustment factor value for that time of day). The pre-adjustment factor may also be determined based on the relationship between the anomalous adjustment factors and the reference adjustment factors (e.g., the average adjustment factor value for that time of day). Any residual glucose amount following the pre-adjustment may be utilized to modify or otherwise adjust the pre-adjustment factor for subsequent deliveries, or to otherwise adjust the carbohydrate ratio in a manner that accounts for the pre-adjustment. Similarly, when boluses associated with a particular event (e.g., exercise) exhibit an anomalous adjustment factor, the carbohydrate ratio may be pre-adjusted in response to an indication of that event to avoid a post-prandial glucose excursion. For example, a user may input or otherwise provide an indication of having engaged in exercise (or alternatively, exercise may be detected using an acceleration sensing arrangement, heart rate monitoring, or other means supported by the infusion device), and in response, the carbohydrate ratio may be adjusted to account for the exercise prior to delivering a bolus. Again, any residual glucose amount following the pre-adjustment may be utilized to modify or otherwise adjust the amount of pre-adjustment for subsequent deliveries, or to otherwise adjust the carbohydrate ratio in a manner that accounts for the pre-adjustment.

For example, the infusion device may store or otherwise maintain a set of historical data including the input carbohydrate amounts to be bolused for along with their associated context information (which may include meal or carbohydrate type identifiers) and adjustment factors (or residual glucose amounts). The infusion device may then analyze the historical data set to identify a pattern or trend associated with a particular bolus context. For example, the infusion device may identify that at a particular time of day on a particular day of the week, there is a pattern of a positive residual glucose amount for a particular input carbohydrate amount and/or a particular meal (or carbohydrate) type when a particular carbohydrate ratio value (or range thereof) is utilized. Based on the trend indicating the pattern of under-bolusing for that particular type of meal and/or input carbohydrate amount at that particular day and time (e.g., by the user habitually underestimating their carbohydrate consumption), when the current carbohydrate ratio value is equal to or within the range of values that result in under-bolusing, the infusion device preemptively adjusts the carbohydrate ratio value based on the historical data set. For example, the amount of pre-emptive adjustment to the carbohydrate ratio value may be based on the average residual glucose amount associated with previous boluses for that combination of input carbohydrate amount and bolus context. Thus, when the infusion device recognizes a combination of input carbohydrate amount and bolus context that matches a detected pattern of under-bolusing, the infusion device may automatically pre-emptively adjust the carbohydrate ratio prior to the blousing in an attempt to prevent postprandial hyperglycemia. Additionally, any residual glucose amount may be stored or otherwise maintained in association with the input carbohydrate amount, the bolus context, and the pre-emptively adjusted carbohydrate ratio (or alternatively, the amount of pre-emptive adjustment), which, in turn, may be utilized by the infusion device to tune, adjust, or otherwise adapt future pre-emptive adjustments based on the effectiveness of preceding pre-emptive adjustments.

As another example, the infusion device may identify that at a particular time of day on a particular day of the week, there is a pattern of a positive residual glucose amount independent of the input carbohydrate amount, the meal type, or the carbohydrate ratio value, for example, due to a pattern of the user experiencing high stress levels at that time, which may be corroborated by the infusion device receiving or otherwise measurements of the user's heart rate, heart rate variability, galvanic skin response, or the like. Thus, in response to a bolus initiated at or around that combination of time of day and day of week that matches the detected pattern, the infusion device may automatically pre-emptively adjust the carbohydrate ratio prior to the blousing in an attempt to prevent postprandial hyperglycemia. In this regard, in some embodiments, to verify the current bolus context matches that of the detected pattern, the infusion device may analyze a current heart rate of the user, a current heart rate variability metric for the user, the current galvanic skin response measurement of the user, or the like, to verify the current bolus conforms to the pattern prior to pre-emptively adjusting the carbohydrate ratio.

As yet another example, in some embodiments, the infusion device may utilize heart rate measurements, acceleration measurements (e.g., from an integrated accelerometer), or other measurements indicative of physical activity to detect or otherwise identify patterns in the residual glucose amount that are correlative to the type and/or intensity of physical activity in association with other bolus context information, and in response, pre-emptively adjust the carbohydrate ratio for a bolus initiated during, around, or after such activity to account for the physical activity. Thus, there are numerous different ways the infusion device can detect a pattern or relationship between the user's residual glucose amounts and their associated bolus information and context, and based thereon, preemptively adjust the carbohydrate ratio as needed to mitigate any potential postprandial hyperglycemia or hypoglycemia.

For the sake of brevity, conventional techniques related to glucose sensing and/or monitoring, bolusing, meal boluses or correction boluses, insulin sensitivity factors, carbohydrate ratios, and other functional aspects of the subject matter may not be described in detail herein. In addition, certain terminology may also be used in the herein for the purpose of reference only, and thus is not intended to be limiting. For example, terms such as "first", "second", and other such numerical terms referring to structures do not imply a sequence or order unless clearly indicated by the context. The foregoing description may also refer to elements or nodes or features being "connected" or "coupled" together. As used herein, unless expressly stated otherwise, "coupled" means that one element/node/feature is directly or indirectly joined to (or directly or indirectly communicates with) another element/node/feature, and not necessarily mechanically.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. For example, the subject matter described herein is not necessarily limited to the infusion devices and related systems described herein. Moreover, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application. Accordingly, details of the exemplary embodiments or other limitations described above should not be read into the claims absent a clear intention to the contrary.

What is claimed is:

1. A method of operating an infusion device to deliver fluid to a body of a user, the method comprising:
    identifying, based on measurement values for a physiological condition in the body of the user, a residual value for the physiological condition resulting from a bolus amount of the fluid delivered by the infusion device, wherein the physiological condition is influenced by the fluid delivered by the infusion device and the bolus amount is influenced by an initial ratio associated with the user, the initial ratio being stored in a data storage element onboard the infusion device;
    converting the residual value to a residual amount of the fluid;
    determining an updated ratio by multiplying the initial ratio by a ratio of the bolus amount to a sum of the bolus amount and the residual amount to compensate for the residual value; and
    storing the updated ratio in the data storage element, wherein a subsequent bolus amount is influenced by the updated ratio.

2. The method of claim 1, wherein identifying the residual value comprises:
    identifying an initial measurement value for the physiological condition corresponding to delivery of the bolus amount;
    identifying a post-prandial settling value from among the measurement values following the delivery of the bolus amount; and
    determining the residual value as a difference between the post-prandial settling value and the initial measurement value.

3. The method of claim 1, wherein converting the residual value to the residual amount of the fluid comprises:
    obtaining a fluid sensitivity factor associated with the user; and
    dividing the residual value by the fluid sensitivity factor to obtain the residual amount of the fluid.

4. The method of claim 1, the fluid comprising insulin, the physiological condition comprising a glucose level, and the initial ratio comprising an initial carbohydrate ratio, the method further comprising:
    receiving, via a user interface, an input amount of carbohydrates; and
    determining the bolus amount of insulin by dividing the input amount by the initial carbohydrate ratio, wherein:
        identifying the residual value comprises identifying a residual glucose value; and
        determining the updated ratio comprises determining an updated carbohydrate ratio by adjusting the initial carbohydrate ratio to compensate for the residual glucose value.

5. The method of claim 4, further comprising:
    receiving, via the user interface, a subsequent input amount of carbohydrates; and
    determining the subsequent bolus amount of insulin by dividing the subsequent input amount by the updated carbohydrate ratio.

6. The method of claim 1, further comprising:
    identifying a current delivery context; and
    identifying the initial ratio associated with the current delivery context from among a plurality of different ratios associated with a plurality of different delivery contexts stored in the data storage element.

7. The method of claim 6, wherein identifying the current delivery context comprises identifying a current time that corresponds to a time window associated with the initial ratio.

8. The method of claim 1, further comprising:
    identifying a current delivery context; and
    identifying the initial ratio associated with the current delivery context from among a plurality of different ratios associated with a plurality of different delivery contexts stored in the data storage element.

9. The method of claim 8, wherein identifying the current delivery context comprises identifying a current time that corresponds to a time window associated with the initial ratio.

10. A method of operating an infusion device to deliver fluid to a body of a user, the method comprising:
    identifying, based on measurement values for a physiological condition in the body of the user, a residual value for the physiological condition resulting from a bolus amount of the fluid delivered by the infusion device, wherein the physiological condition is influenced by the fluid delivered by the infusion device and the bolus amount is influenced by an initial ratio associated with the user, the initial ratio being stored in a data storage element onboard the infusion device;
    converting the residual value to a residual amount of carbohydrates, the bolus amount being influenced by the initial ratio and an input amount of carbohydrates;
    determining an updated ratio to compensate for the residual value by multiplying the initial ratio by a ratio of a difference between the input amount and the residual amount to the input amount; and
    storing the updated ratio in the data storage element, wherein a subsequent bolus amount is influenced by the updated ratio.

11. The method of claim 10, wherein identifying the residual value comprises:
    identifying an initial measurement value for the physiological condition corresponding to delivery of the bolus amount;
    identifying a post-prandial settling value from among the measurement values following the delivery of the bolus amount; and
    determining the residual value as a difference between the post-prandial settling value and the initial measurement value.

12. The method of claim 10, the fluid comprising insulin, the physiological condition comprising a glucose level, and the initial ratio comprising an initial carbohydrate ratio, the method further comprising:
    receiving, via a user interface, an input amount of carbohydrates; and
    determining the bolus amount of insulin by dividing the input amount by the initial carbohydrate ratio, wherein:
        identifying the residual value comprises identifying a residual glucose value; and
        determining the updated ratio comprises determining an updated carbohydrate ratio by adjusting the initial carbohydrate ratio to compensate for the residual glucose value.

13. The method of claim 12, further comprising:
    receiving, via the user interface, a subsequent input amount of carbohydrates; and
    determining the subsequent bolus amount of insulin by dividing the subsequent input amount by the updated carbohydrate ratio.

14. A method of operating an infusion device to deliver insulin to a body of a user, the method comprising:
    receiving, via a user interface, an input amount of carbohydrates;
    determining a bolus amount of insulin by dividing the input amount by an initial carbohydrate ratio stored in a data storage element onboard the infusion device;
    identifying, based on measurement values for a glucose level of the user, a residual glucose value resulting from the bolus amount of insulin delivered by the infusion device, wherein the glucose level is influenced by the insulin delivered by the infusion device;
    converting the residual glucose value to a residual carbohydrate amount;
    determining an updated carbohydrate ratio by scaling the initial carbohydrate ratio based on a relationship between the residual carbohydrate amount and the input amount of carbohydrates to compensate for the residual glucose value; and
    storing the updated carbohydrate ratio in the data storage element, wherein a subsequent bolus amount is influenced by the updated carbohydrate ratio.

* * * * *